US00RE34782E

United States Patent [19]

Dandliker et al.

[11] E Patent Number: Re. 34,782

[45] Reissued Date of Patent: Nov. 8, 1994

[54] FLUOROMETER

[75] Inventors: Walter B. Dandliker; Howard S. Barr, both of Escondido; Henry S. Katzenstein, Pacific Palisades, all of Calif.; Keith R. Watson, Baja California, Mexico

[73] Assignee: Diatron Corporation, San Diego, Calif.

[21] Appl. No.: 969,794

[22] Filed: Oct. 12, 1992

Related U.S. Patent Documents

Reissue of:

[64] Patent No.: 4,877,965
Issued: Oct. 31, 1989
Appl. No.: 751,746
Filed: Jul. 1, 1985

U.S. Applications:

[63] Continuation of Ser. No. 611,929, Nov. 13, 1990, abandoned.

[51] Int. Cl.[5] ..... G01N 21/64

[52] U.S. Cl. ..... 250/458.1; 250/461.2; 356/318

[58] Field of Search ..... 250/458.1, 461.2; 356/318

[56] References Cited

U.S. PATENT DOCUMENTS

| | | | |
|---|---|---|---|
| 2,071,408 | 2/1937 | Jones | 350/523 |
| 3,835,247 | 9/1974 | Soames | 358/139 |
| 4,006,360 | 2/1977 | Mueller | 250/461.2 |
| 4,259,574 | 3/1981 | Carr et al. | 250/302 |
| 4,336,459 | 6/1982 | Fay | 250/459.1 |
| 4,341,957 | 7/1982 | Wieder | 250/461.2 |
| 4,442,455 | 4/1984 | Huignard et al. | 358/209 |
| 4,486,776 | 12/1984 | Yoshida | 358/106 |
| 4,786,170 | 11/1988 | Groebler | 356/318 |
| 4,791,310 | 12/1988 | Honig et al. | 250/458.1 |

FOREIGN PATENT DOCUMENTS

| | | | |
|---|---|---|---|
| 2532756 | 3/1984 | France | 250/458.1 |
| 3502059 | 11/1985 | Germany . | |

*Primary Examiner*—Constantine Hannaher
*Attorney, Agent, or Firm*—Ellsworth R. Roston; Charles H. Schwartz

[57] ABSTRACT

A fluorometer for measuring a particular fluorescence emanating from a specimen and operating in accordance with the following method. Producing a burst of concentrated light energy and directing the concentrated light energy toward the specimen to produce a fluorescence from the specimen including the particular fluorescence. Preferably producing an image of the fluorescence. Detecting the fluorescence and producing a signal in accordance with the fluorescence. Controlling the passage of the image of the fluorescence for detecting within a particular time period so as to optimize the detection of the particular fluorescence. Timing the operation to sequence the detection of the fluorescence within the particular time period after the production of the burst of concentrated light energy. Scanning the fluorescence from the specimen for forming signals representative of the fluorescence from the specimen. Analyzing the signals to enhance the portion of the signal representing the particular fluorescence relative to the portion of the signal.

123 Claims, 5 Drawing Sheets

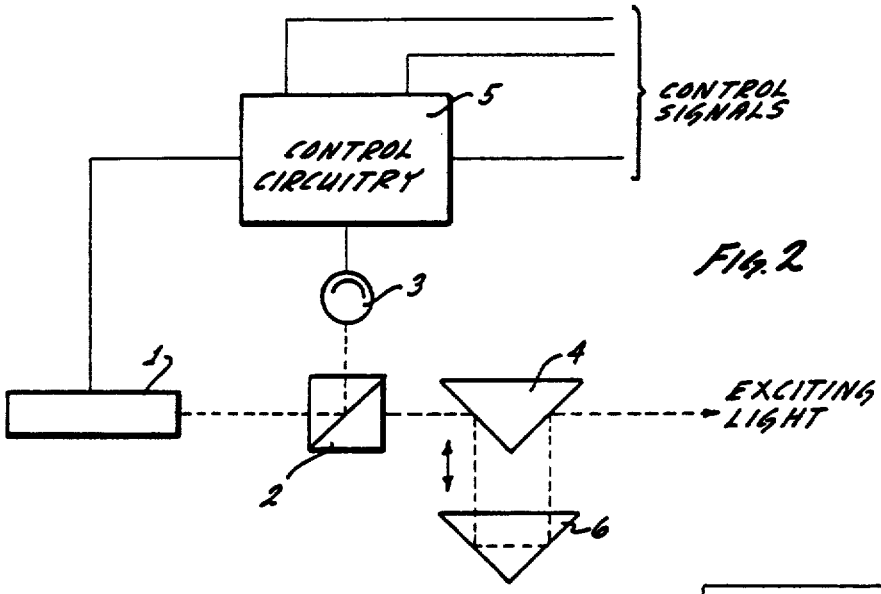
Fig. 2
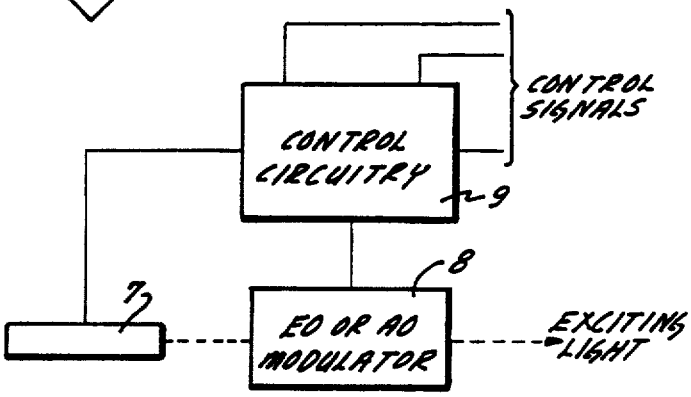
Fig. 3
Fig. 4
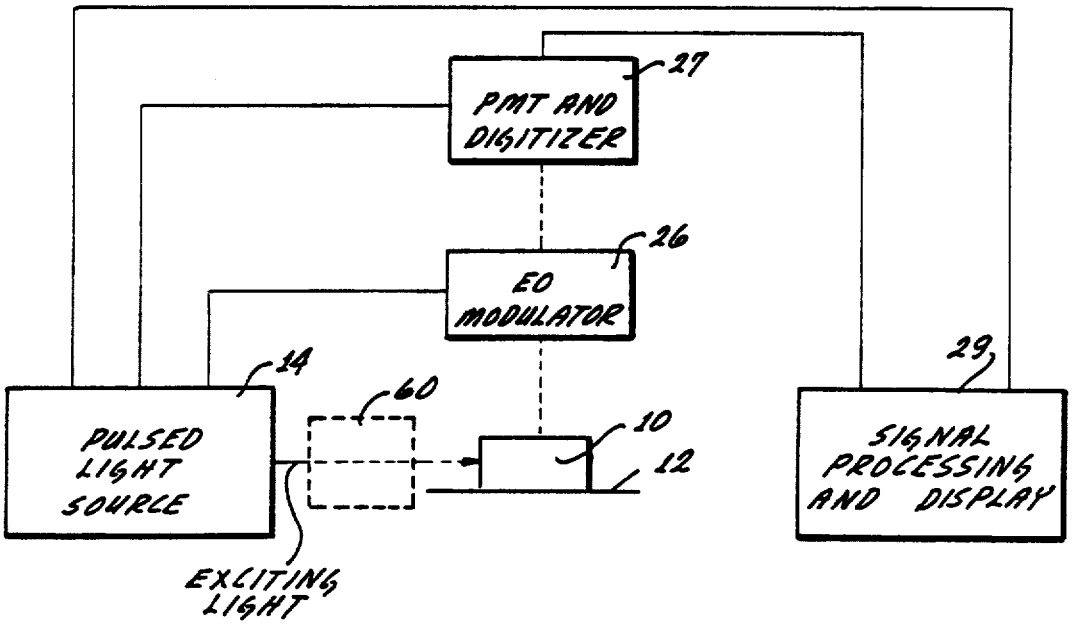

FLUOROMETER

Matter enclosed in heavy brackets [ ] appears in the original patent but forms no part of this reissue specification; matter printed in italics indicates the additions made by reissue.

*This is a continuation of reissue application Ser. No. 07/611,929 filed Nov. 13, 1990 now abandoned.*

BACKGROUND OF THE INVENTION

1. Field of the Invention

The present invention relates to fluorometers for detecting a particular fluorescence from a specimen. Specifically, the present invention relates to a time gated fluorometer for forming an output signal preferably representative of an image of the fluorescent specimen and to a specific method to enhance the analysis of the output signal received to thereby enhance the detection of the particular fluorescence.

2. Description of the Prior Art

In general, prior art fluorometers all suffer from a common problem of providing for a discrimination between the generated fluorescent signal and the background noise. Certain types of conventional fluorometers discriminate between the fluorescent signal and the background noise on the basis of wave length. This type of discrimination is generally not sufficient for many types of fluorescent signals.

Another type of discrimination can be accomplished using a time gated technique. In particular, these instruments are based on the principle of permitting the observation of the fluorescence or luminescence a short, and if desired a variable, time after the excitation period. Time gated fluorometers therefore add an additional level of discrimination by viewing the signal fluorescence during an optimal time window. In the past, this technique generally employed a fluorophore of long decay time in order to allow the background fluorescence to decay.

The time gated technique is in general based on a phosphoroscope invented by Becquerel in 1867. In the Becquerel instrument, the luminescent substance is placed between two rotating discs which are mounted on a common axis and which have sector shaped apertures. The variable time gating is achieved by an adjustment of the angle between a sector on one disc and a sector on the other. Subsequent refinements of the time gating technique have been accomplished by the use of spark discharges, oscilloscopes, Kerr cells and supersonic cells.

The rotating disc invented by Becquerel was put into a conical configuration for a microscope by Jones as described in U.S. Pat. No. 2,071,408 in 1937. Other more recent improvements have used electronic techniques. For example, Wieder, U.S. Pat. No. 4,341,957, provided for the gating of a detecting circuit electronically and used a laser for excitation. In this way, as in other refinements of Becquerel phosphoroscope, the gating mechanism may be adjusted so that observation of the desired signal can be optimized. Other prior art devices such as Mueller, U.S. Pat. No. 4,006,360, use electronic gating to distinguish between species of differing decay time where two species are involved and one is bound dye and the other is an unbound dye.

Two commercial instruments are currently available for the measurement of decay time or lifetimes. Both of these instruments utilize nanosec. flash sources (electric spark in air at reduced pressure). One instrument puts the output of a photomultiplier tube onto a fast ocilloscope. Provision is made to match the experimental curve with a sum of up to 3 or 4 exponentials.

The second instrument excites the sample by repeated flashes from the source (such as at 5 kHz) and pulses the photomultiplier at increasingly longer times after the flash. The output is fed into a recorder or computer and gives an intensity vs. time signal. In addition, this instrument is supplied with software to reconvolute the experimental curve by a well known method termed Linearized Least Squares Reconvolution.

Both wavelength based discrimination and time based discrimination suffer by having background fluorescence superimposed on the signal with only an indirect means of segregating the two. In addition, the use of dyes of long decay time effectively smears out the desired signal over a long time period, thus making this signal hard to extract. Dyes of long decay time have inherently low extinction coefficients and therefore provide inefficient excitation of the fluorescence.

SUMMARY OF THE INVENTION

The present invention is directed to a new type of fluorometer which permits the signal from the fluorophore to be automatically separated from the background in an improved manner to produce an enhanced fluorescent signal. This enhancement of the fluorescent signal occurs by a particular instrument design, by the type of data which is collected and by a specific method used to process this data.

In particular, in a specific embodiment, the invention is implemented using optical time gating wherein the time gating allows high quality optical imaging of the fluorescent source and operates at speeds consistent with the use of common fluorescent labels. This is accomplished using electro-optic modulators which are made of crystals which are cubic and hence isotropic when unstressed. Such modulators operate with large numerical apertures, are fast and therefore are suitable for use in a gated fluorescence microscope version of the present invention. As an example, the modulators may be made of a cubic crystal material such as Cu Cl (cuprous chloride). The use of such electro-optic modulators makes possible the construction of a gated fluorescence microscope in which the optical image is viewed directly such as in normal microscopy.

The use of high quality optical imaging is not necessary if the invention is used only as a fluorometer for detecting the fluorescent signal as opposed to providing a representation of the fluorescent image. However, even in the former case imaging is advantageous since such imaging provides for an efficient collection of light.

In one actual embodiment of the present invention, the fluorometer may be considered to be a one pixel display. The present invention provides for an enhanced optical image of a fluorescent specimen formed from a large number of pixels. In one embodiment a single pulse from a laser is used to excite fluorescence from a microscopic spot on the specimen. The position of the spot on the specimen depends upon the position of a stepping stage all of which is sensed and under the control of control circuitry.

A microscopic objective focuses the light from the excited spot onto a photodetector through an electro-optic modulator or an equivalent structure such as an electronically time gated photodetector. The electro-optic modulator is used as an optical shutter. The electro-optic modulator is designed to have a high numerical aperture to thereby allow the collection of more light over a greater solid angle thereby permitting a higher resolution in the image formation. The present invention also improves the image quality to thereby provide a better signal to noise ratio than other types of electro-optic modulators such as Pockels cells or Kerr cells. In addition, the collection of more light is beneficial to improve the signal to noise ratio relative to a photodetector positioned after the electro-optic modulator. The electro-optic modulator opens at a time $t_\alpha$ after the burst from the laser and closes at a time $t_\beta$. The timing control of the opening and closing of the electo-optic modulator and the control of the laser are provided by the control circuitry.

The fluorescence may be recovered by a photodetector and the recovered information may be stored and processed to extract, from the fluorescence signal, intensity as a function of time, and with the information for the one illuminated spot stored for subsequent display. The stepping stage may now move the specimen to a different spot as directed by the control circuitry and the above process is repeated until the specimen has been scanned as desired to build up a complete enhanced image. If desired, the stored information may be printed out in a numerical form as opposed to providing for an actual image and, in such a generalized case, the instrument of the present invention is characterized as a fluorometer rather than the specialized designation of fluoromicroscope.

In another embodiment of the invention, the image of a large number of pixels is directly transmitted through the electro-optic modulator to a photosensitive array. The array is then scanned to form the complete image of the fluorescence from the specimen.

The advantages present in the apparatus and method of the present invention are based on a number of physical principles which underlie the instrument design and method of operation. In particular, these physical principles include the excitation by a concentrated pulse or burst of light energy provided by the laser which is very short in duration compared to the decay time of the fluorophore of interest. In addition, the excitation provided by the laser produces a light pulse of sufficient energy to excite substantially all of the fluorophore molecules so that substantially all of the fluorescence of interest is at its peak excitation when the burst ends. If the burst is too long, then the fluorescence of interest starts to decay during excitation thereby losing signal and contributing indirectly to photobleaching. If the burst is of insufficient energy then random fluctuations in both the fluorescence photon flux and electrical dark noise become more important and affect measurement of the signal adversely.

The present invention also includes sensing of the fluorescence by means of a photosensitive device gated by an electro-optic modulator to respond promptly after the excitation pulse and arranged to sense the total emission intensity over a large portion of the entire time course of the particular fluorescence being measured. The output of the photosensor is then recorded following the excitation pulse and with this recording provided by suitable fast analog or digital means.

The emission resulting from the excitation pulse is analyzed by a particular method which permits the particular fluorescent signal, which has a characteristic decay time, to be extracted from the time dependence of the total emmission intensity.

The above described conditions assure that the maximum possible fluorophore signal is obtained while minimizing photobleaching or fading. In addition, the output signal from the fluorometer or image of the fluoromicroscope of the present invention ideally consists of signals from the fluorophore only. The degree to which this ideal can be approached depends only upon the accuracy with which the curve of intensity versus time for the particular fluorescence can be sensed and recorded.

The present invention therefore provides for an apparatus and method of enhancing the sensing of particular fluorescent data and with such enhancement provided both by the structural components in the system for detecting the fluorescence, and a method of analysis of the fluorescent signal when detected.

BRIEF DESCRIPTION OF THE DRAWINGS

A clearer understanding of the present invention will be had with reference to the following descriptions and drawings wherein:

FIG. 2 illustrates a first embodiment of a pulsed light source;

FIG. 3 illustrates a second embodiment of a pulsed light source;

FIG. 4 illustrates a first embodiment of a fluorometer exemplifying instruments which may be formed as a measurement tool;

DESCRIPTION OF THE PREFERRED EMBODIMENTS

Fluorescent molecules are used as a label or tracer for a number of reasons and in particular have been used in the medical field. In general, the main problem of obtaining the fluorescent signal from the fluorescent molecule is to separate or segregate the desired signal from the unwanted background fluorescence.

Figure 1:
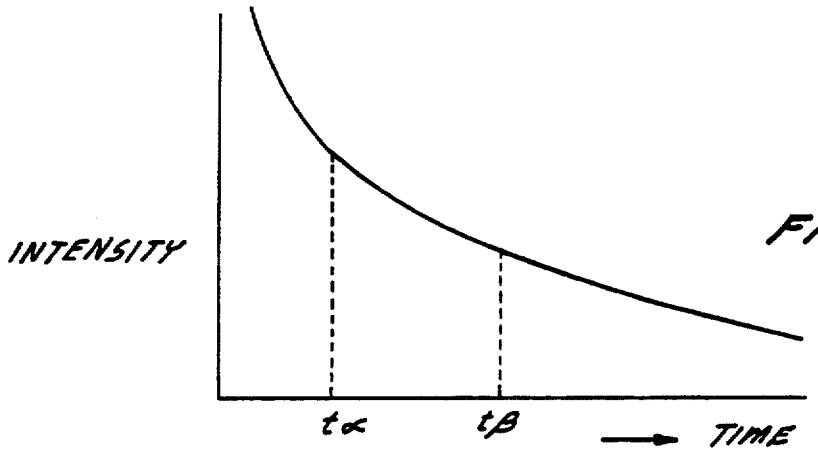
FIG. 1 illustrates a generalized fluorescent decay curve after excitation of a fluorescent specimen.

In general, two different characteristics may be used to separate the desired signal from the background. In particular, wave length characteristics and decay time characteristics of the emitting fluorescent molecules can be used to implement the separation between signal and background. As shown in FIG. 1, once the fluorescent molecules have been illuminated, such as by a laser pulse, the decay of the fluorescence from the assembly of molecules having a number of different decay times provides a time course of intensity versus time of the general character shown in FIG. 1.

Using the concept of a time window described above, the fluorescence may be observed between $t_\alpha$ and $t_\beta$ where $t_\alpha$ and $t_\beta$ are in the general region of the decay time for the particular label being measured. If the fluorescent signal is observed only during this particular time window, the signal from the label is enriched since rapidly decaying fluorescence in the background, not associated with the label, will not be sensed and slowly decaying fluorescence, again not associated with the label, will be cut off after the time window. The excited states of all of the molecules begin to decay immediately but the long decay time or slowly decaying fluorescence is spread out over a longer interval than the short decay time or rapidly decaying fluorescence.

The present invention also provides for a method which may be designated as Hybrid Laplace Transform Amplitude Analysis, or amplitude analysis for short, for extracting a known decay fluorescent component ($\tau_x$) from a noise background containing a multitude of different components ($\tau_1 \ldots \tau_N$). By this method the decay curve is analyzed by differentiating the decay curve at N points (where N is the number of fluorescent components in the background) and by integrating over N intervals along the decay curve. By this particular method a sufficient number of equations is obtained to solve uniquely the desired particular fluorescent signal.

The method may be carried out over the entire time course of the fluorescent decay or over a selected time window as described above in which the signal has been enriched. Depending upon the particular fluorescence being analyzed, one or the other of the time periods may give the more rapid and incisive convergence to a final value of N and the unknown particular fluorescent defined as $I_x(0)$.

It is to be appreciated that the methods of the present invention can be used in conjunction with well known methods of wavelength discrimination.

Given a total fluorescence signal $I_s(t)$ as a function of time, represented by a sum of unknown signals as well as the desired signal $$I_x(0)e^{-k_x t},\ k_x = T_x^{-1}$$

where $$I_s(t) = I_x(t) + \sum_{i=1}^{N} I_i(t) \tag{1}$$

$$= I_x(0)e^{-k_x t} + \sum_{i=1}^{N} I_i(0)e^{-k_i t} \tag{2}$$

We need to evaluate $I_x(0)$. Notice that we know $I_s(t)$ for all time. We known the characteristic decay time ($T_\chi = k_x^{-1}$) of the fluorescent label. We DO NOT known $I_i(0)$, $k_i$ and wish to evaluate $I_x(0)$. Hence we have (2N+1) unknowns. This requires (2N+1) equations for a unique solution. We obtain one equation from equation (2) at t=0 namely $$I_s(0) = I_x(0) + \sum_{i=1}^{N} I_i(0) \tag{3}$$

By differentiating equation (2) at N points and by integrating equation (2) over N intervals we can solve for $I_x(0)$. Consider, for example, just one background noise term, say, $$I_1(0)e^{-k_1 t}$$

Applying the above technique, we get $$I_s(t) = I_x(0)e^{-k_x t} + I_1(0)e^{-k_1 t} \tag{4}$$

Differentiating equation (4) with respect to t we get:

$$\Gamma_s(t) = -k_x I_x(0)e^{-k_x t} - k_1 I_1(0)e^{-k_1 t} \tag{5}$$

Integrating equation (4) from 0 to infinity we obtain:

$$I(0, \infty) = \left[\frac{-I_x(0)e^{-k_x t}}{k_x} - \frac{I_1(0)e^{-k_1 t}}{k_1}\right]_0^{\infty} \tag{6}$$

Evaluate equation (4) and (5) at t=0 to give:

$$I_s(0) = I_x(0) + I_i(0) \tag{7}$$

$$\Gamma_s(0) = -k_x I_x(0) - k_1 I_i(0) \tag{8}$$

Substituting limits into equation (6)

$$I(0, \infty) = \frac{I_x(0)}{k_x} + \frac{I_1(0)}{k_1} \tag{9}$$

We now have three equations, (7), (8) and (9), in three unknowns, $I_x(0)$, $I_i(0)$ and $k_1$. Next, eliminate $I_1(0)$ by multiplying equation (7) by $k_1$ and adding to equation (8), dropping (0)'s to give equation (12)

$$k_1 I_s = k_1 I_x + k_1 I_1 \tag{10}$$

$$\Gamma_s = -k_x I_x - k_1 I_1 \tag{11}$$

$$k_1 I_s + \Gamma_s = k_1 I_x - k_x I_x \tag{12}$$

Solving equation (12) for $k_1$ gives:

$$k_1 = \frac{k_x I_x + \Gamma_s}{I_x - I_s} \tag{13}$$

Substitute this value of $k_1$ from equation (13) into equation (9):

$$I = \frac{I_x}{k_x} + I_1\left(\frac{I_x - I_s}{k_x I_x + \Gamma_s}\right) \tag{14}$$

For $I_1$ substitute the value from equation (7) giving:

$$I = \frac{I_x}{k_x} + (I_s - I_x)\left(\frac{I_x - I_s}{k_x I_x + \Gamma_s}\right) \tag{15}$$

Rearranging and solving for $I_x$ gives finally $$I_x = \frac{k_x(I_s^2 + I\Gamma_s)}{\Gamma_s + k_x(2I_s - k_x I)} \tag{16}$$

The time window technique method may be combined advantageously with the amplitude analysis method described above in treating particular fluorescent data. This is because the underlying assumption in the analysis is that the observed decay curve (intensity versus time) consists of a sum of independent exponential curves one from the label (x) and N curves arising from the N components in the background. Thus, the intensity $I_s$ observed from the entire sample is equation (1) above. The function $I_s(t)$ may be measured directly after a single excitation pulse or it may be deduced from several values of $$\int_0^t I_s(t)dt$$

which is evaluated by an integrating detector after each of several excitation pulses.

Since the decay of all components in the fluorescence is assumed to be exponential, zero time is arbitrary and may be taken at any point along the curve shown in FIG. 1. Therefore any zero time associated with equation (2) results in equation (3) as shown above.

Equation (2) may be differentiated as follows:

$$\Gamma_s(t) = -k_x I_x(0)e^{-k_x t} + \sum_{i=1}^{N} -k_i I_i(0)e^{-k_i t} \tag{17}$$

Evaluation of Equation (17) at N different points $t_1$ to $t_N$ gives N independent equations. Integration of equation (2) over N different intervals gives an additional N equations, for example:

$$I(0, t_1) = \left[\frac{I_x(0)e^{-k_x t}}{-k_x} + \sum_{i=1}^{N} \frac{I_i(0)e^{-k_i t}}{-k_i}\right]_0^{t_1}. \tag{18}$$

The 2N+1 equations are sufficient to solve for $I_x(0)$ by eliminating the N different k's and the N different $I_i(0)$'s. A numerical solution for $I_x(0)$ is accomplished by carrying out a series of computations for different N's e.g. N=1, N=2 etc. When the results of the (n+1)th computation are not significantly different from the nth computation, the process is stopped and that value of $I_x(0)$ is taken as the result.

A second method for the extraction of signal may be termed Normalized Background Analysis (NBA). In this method a background measurement is made on an unlabeled or unstained blank sample of material which is otherwise similar to a sample which is stained or to be stained. In the usual type of background measurement, the blank or unlabeled sample must be identical in both size and fluorescence characteristics to the labeled sample except that no added label is present. In the NBA method the only requirement is that the background be measured on the same type of material but the amount need not be the same. This feature is of particular importance, e.g., in measuring the total amount of label taken up by a sample of tissue or by a group of cells in the field of a fluorescence microscope. In such a situation, it is not feasible to prepare a blank identical in size to the stained sample and unless the specimen is fixed it is not feasible to measure before and after staining.

The NBA method may be developed as follows. As before, the background itensity, $I_b$, is assumed to consist of a sum of intensities with exponential decays:

$$I_b(t) = \sum_{i=1}^{N} I_i(0)e^{-k_i t} \tag{19}$$

The emission from the stained sample is then of the form:

$$I_s(t) = I_x(0)e^{-k_x t} + \alpha \sum_{i=1}^{N} I_i(0)e^{-k_i t} \tag{20}$$

The factor, $\alpha$, provides for the fact that the amount of sample material in the blank and sample measurements may be different. Writing equation (20) in a more compact form $$I_s(t) = \alpha I_b(t) + I_x(t) \tag{21}$$

Differentiating gives $$\Gamma_s(t) = \alpha \Gamma_b(t) + \Gamma_x(t) \tag{22}$$

Eliminating $\alpha$ from equations (21) and (22) gives:

$$I_s\Gamma_b - \Gamma_s I_b = I_x\Gamma_b - I_b\Gamma_x \tag{23}$$

Since $$I_x = I_x(0)e^{-k_x t} \tag{24}$$

$$\Gamma_x = -k_x I_x(0)\, e^{-k_x t} = -k_x I_x \tag{25}$$

Substituting equation (25) into equation (23) and solving for $I_x$ gives:

$$I_x = \frac{I_s\Gamma_b - \Gamma_s I_b}{\Gamma_b + I_b k_x} \tag{26}$$

true for all t.

FIG. 2 illustrates a first embodiment of a pulsed light source for use with the various fluormeters formed as embodiments of the present invention. In FIG. 2 a laser 1 directs light energy to a beam splitter 2. A first portion of the energy from the beam splitter is directed to a photodetector 3 and a second portion is directed to a first prism 4. The photo detector 3 produces an output signal when the laser is on and such signal is coupled to control circuitry 5.

Control signals are also applied to the control circuitry 5 so that the laser 1 may be controlled "on" and "off" to produce a burst of light energy of a desired short duration as described above. A second prism 6 is positioned to receive light energy from the first prism 4 and to redirect the light energy back to the first prism 4. The distance between the prisms 4 and 6 may be varied to provide a variable optical time delay so that the burst energy is in proper phase with an optical shutter and/or detector which would be part of a complete instrument.

FIG. 3 illustrates a second embodiment of a pulsed light source for use with the various flurometers formed as embodiments of the present invention. In FIG. 3, a continuous wave or wide pulse source 7 of light directs light energy to a modulator 8. The light source is nearly collimated, monochromatic and polarized and is thereby similar to the output from a laser. The modulator 8 forms an optical shutter under the control of control circuitry 9 to produce a short burst of high energy exciting light from the modulator 8. The modulator 8 may be formed by an electro-optic modulator or an acousto-optic (AO) modulator.

FIG. 4 is a first embodiment of a fluorometer forming a measurement tool. In FIG. 4 a specimen 10 to be analysed is positioned on a surface 12. A pulsed light source 14, which may be either the light source formed by the embodiment of FIG. 2 or the embodiment formed by the embodiment of FIG. 3 directs a burst of exciting light to the specimen 10.

The light energy from the light source 14 excites fluorescence in the specimen. The excited fluorescence emits energy which is directed to an electro-optic modulator 26 so as to produce a time gating of the emitted flourescence. The timing control may be provided from a control signal from the control circuitry 5 or 9 of the pulsed light sources shown in FIG. 2 and 3. The electro-optic modulator 26 is controlled to open at a time $t_\alpha$ after the burst from the light source and to close at a time $t_\beta$, as shown in FIG. 1. The emitted fluorescence is therefore directed to a photomultiplier and digitizer 27 to detect and digitize the output emitted fluorescence only between the times $t_\alpha$ and $t_\beta$.

The output from the photomultiplier and digitizer 27 is then coupled to a signal processing and display unit 29 to analyze the information in accordance with the methods described above and to display the results of this analysis. It is to be appreciated that the methods of analysis may be used with a short period time gated fluorescence output but may also be used for analysis over a longer time period. Also, the electro-optic modulator 26 could be eliminated and the emitted fluorescence from the specimen 10 could be directly applied to the photomultiplier and digitizer 27 if the photomultiplier is gated by electronic means.

Figure 5:
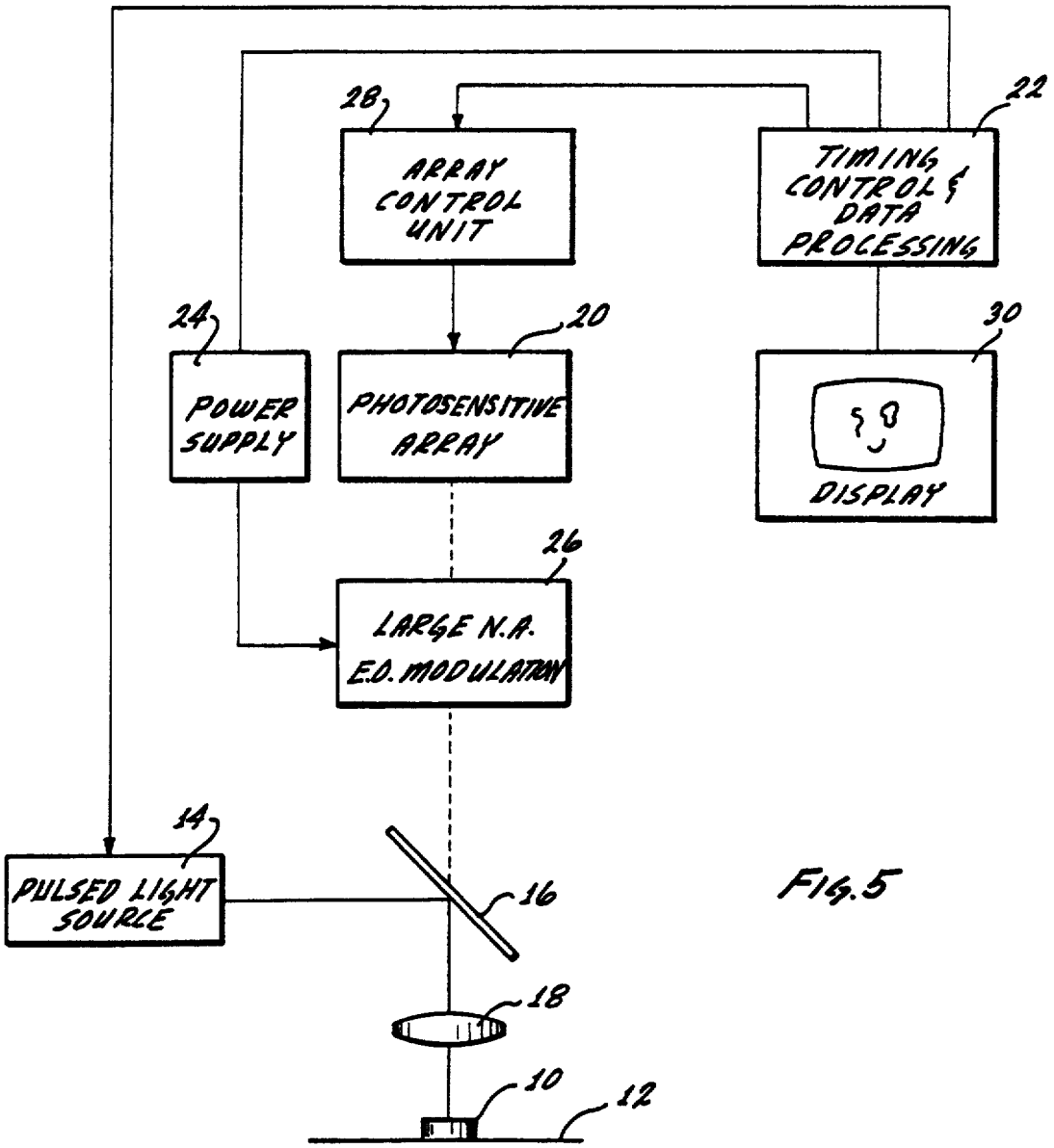
FIG. 5 illustrates a second embodiment of a fluorometer exemplifying instruments which may be formed as a fluoromicroscope and with a photosensitive array.

FIG. 5 illustrates a first embodiment of a fluorescence microscope exemplifying instruments which may be formed by incorporating an electro-optic modulator and which may incorporate the methods of analysis described above. As shown in FIG. 5, the specimen 10 to be analyzed is positioned on the stationary surface 12. A pulsed light source 14 is controlled to direct a pulse or burst of concentrated light energy toward a dichroic mirror 16. The mirror 16 directs the light energy through an objective lens 18 to the specimen 10. Light filters may be added in the excitation and emission beams to thoroughly isolate the fluorescence emission and to limit excitation to a single or narrow band of wavelengths.

The light energy from the source 14 excites fluorescence in the specimen. The excited fluorescence thereby produces a fluorescent pattern on the specimen 10. The objective lens 18 forms an image of the fluorescent specimen at a photo sensitive array 20 beginning at the time $t_\alpha$ after the pulse from the source 14. This time $t_\alpha$ is determined by control circuitry forming part of a timing control and data processing module 22. The control circuitry actually controls a power supply 24 which in turn controls the operation of the electro-optic modulator 26. The electro-optic modulator is therefore opened at the time $t_\alpha$ to allow the image of the fluorescent specimen to be passed to the photo sensitive array 20.

At time $t_\beta$ the electro-optic modulator 26 closes so that the photosensitive array has detected, at a plurality of elements in the array, information representing the time integral of the intensity of the fluorescence decay from time $t_\alpha$ to time $t_\beta$ after the flash of the light source 14. It is to be appreciated that the time interval between $t_\alpha$ to $t_\beta$ may be a time window having a relatively short duration as described above or may extend out over the entire time course of the fluorescent decay. The particular time interval chosen would be dependent upon the particular type of specimen being observed. An array control unit 28 scans each element of the array after the electro-optic modulator 26 closes and for each element of the array, the array control unit 28 records the time integral of the intensity from $t_\alpha$ to $t_\beta$.

The module 22 includes a data processing portion and this portion stores the data and then analyzes the stored data in accordance with the methods described above to extract the desired particular fluorescent signal from the total intensity stored signal. The particular fluorescent signal is then used to produce an output indication such as a signal image on a display 30 and with this signal image representing the desired particular fluorescent signal from the specimen 10.

A photosensitive array or multiple detector may be used in two distinctly different modes for fluorescence measurements. In one, all of the elements of the array view the same point but can be used to generate, over the time course of the signal, different mathematical properties of the signal. These properties may be combinations of the intensity, its derivatives or integrals. In another mode each photosensitive element derives the same type of information but for a different point in an image of the fluorescent sample. In this mode, the sample may have to be excited multiple times in order to obtain the required amount of information to solve equation (2).

It is to be appreciated that the specific embodiment of a fluoromicroscope illustrated in FIG. 5 is illustrative only and that various adaptations and modifications may be made. For example, an image tube may be used in place of the photosensitive array and the image of the fluorescence viewed directly by an observer or by a camera or with a direct observation by an observer or through a camera without any intervening detectors. Also, the EO modulator can be omitted if the photosensitive array or image tube is gated by electronic means.

Figure 6:
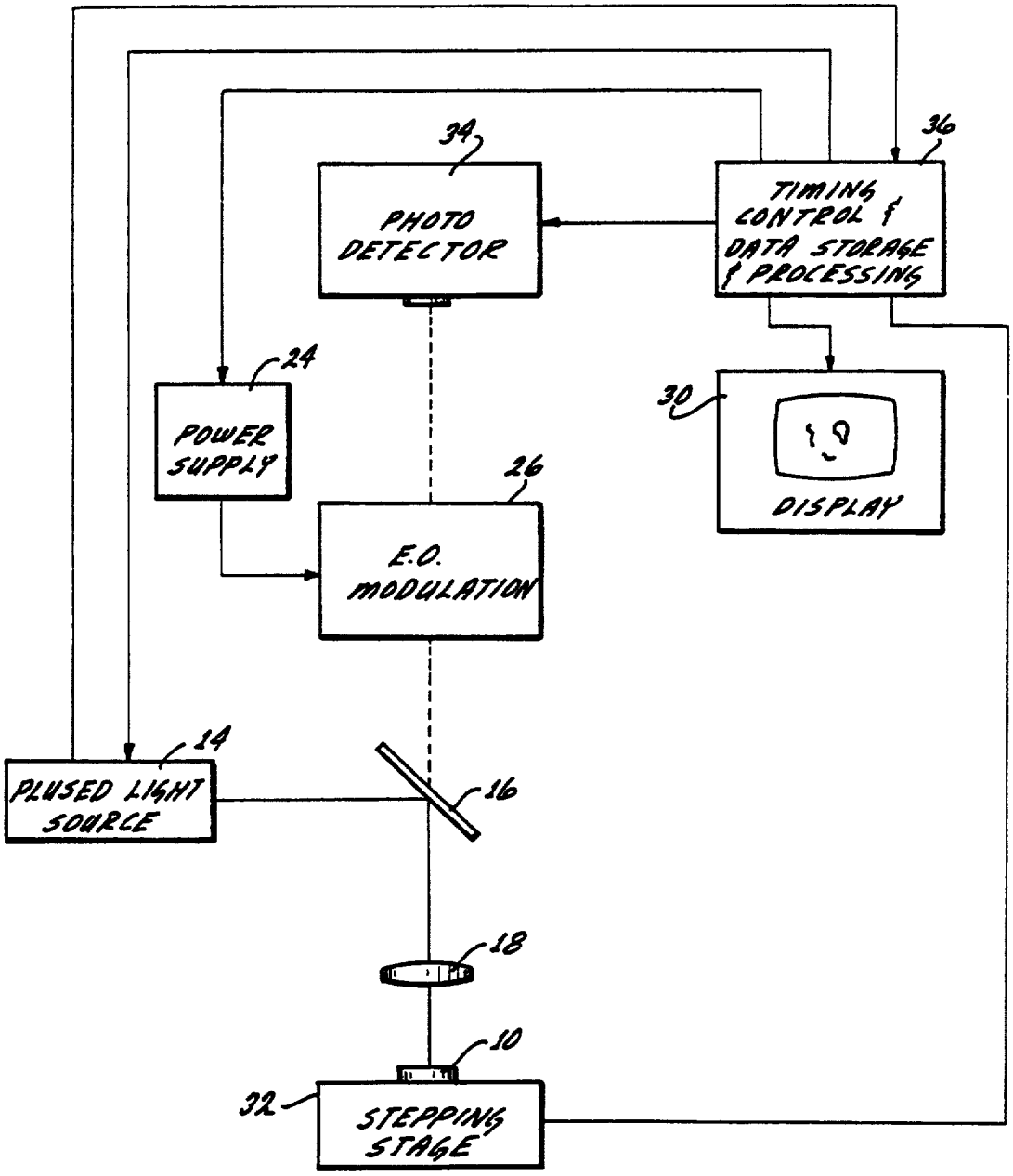
FIG. 6 illustrates a third embodiment of a fluorometer exemplifying instruments which may be formed as a fluoromicroscope and with a stepping stage.

FIG. 6 illustrates a fluoromicroscope exemplifying instruments which may be formed using a stepping stage. Portions of the system of FIG. 6 similar to those shown in FIG. 4 and 5 are given the same reference character. Specifically, in FIG. 6 the specimen 10 is mounted on a stepping stage 32. The stepping stage is assumed to be initially at a first position. The light source 14 is controlled to produce a pulse or burst of light energy to excite fluorescence from a single microscopic spot on the specimen 10. The light source 14 directs the light energy to the specimen 10 by reflecting the light energy from the mirror 16 and through the lens 18. The objective lens 18 focuses the fluorescence from the excited spot on the specimen 10 to a photodetector 34. The actual control of the fluorescence detected by the photodetector 34 is in accordance with the opening and closing of the electro-optic modulator 26.

The electro-optic modulator opens at a time $t_\alpha$ after the laser flash and closes at a time $t_\beta$. As described above, the time interval may be a short duration time window or may be a period of time sufficiently long to encompass a large fraction of the entire time course for the fluorescence decay. A module 36 provides timing control, data storage and processing. Specifically, as in the embodiment of FIG. 5, the light source is controlled to produce the pulse of light energy. At a predetermined period of time after the pulse, the electro-optic modulator 26 is controlled through the power supply to open and close and thereby act as a shutter. The information detected by the photodetector represents the intensity as a function of time for the one illuminated spot on the specimen. This information is stored by the module 36.

Additionally, the module provides for processing of this stored data from the photodetector in accordance with the methods of analysis described above to separate the desired particular fluorescent signal from the background fluorescence. The information may then be displayed in the display 30 and with the displayed information representing the information for a large number of spots on the specimen. In particular, the stepping stage 32 is controlled to repetitively step to different spots. This stepping is under the control of the control circuitry in the module 36. After each step, the illumination of a spot is provided by the light source 14 and with a subsequent extraction of the fluorescent signal. The process is repeated until the specimen has been scanned in a desired pattern to produce the output display.

It is to be appreciated that the specific embodiment of fluoromicroscope illustrated in FIG. 6 is illustrative only and that various adaptations and modifications may be made. For example, the EO modulator may be omitted if the photodetector is gated by electronic means.

Figure 7A:
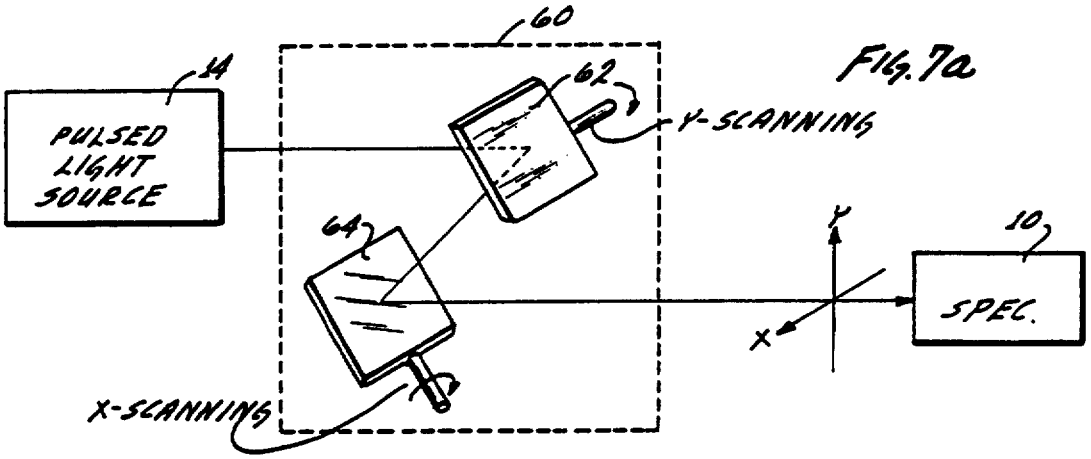
FIGS. 7 (a), (b) and (c) illustrate various alternative structures for providing direct scanning of the specimen for producing X-Y movement of the beam from the pulsed light source.
Figure 7B:
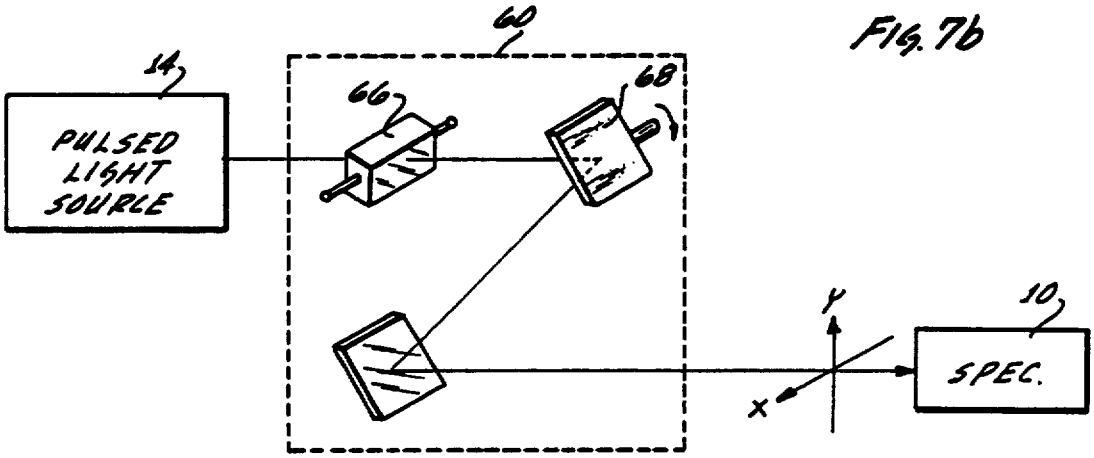
Figure 7C:
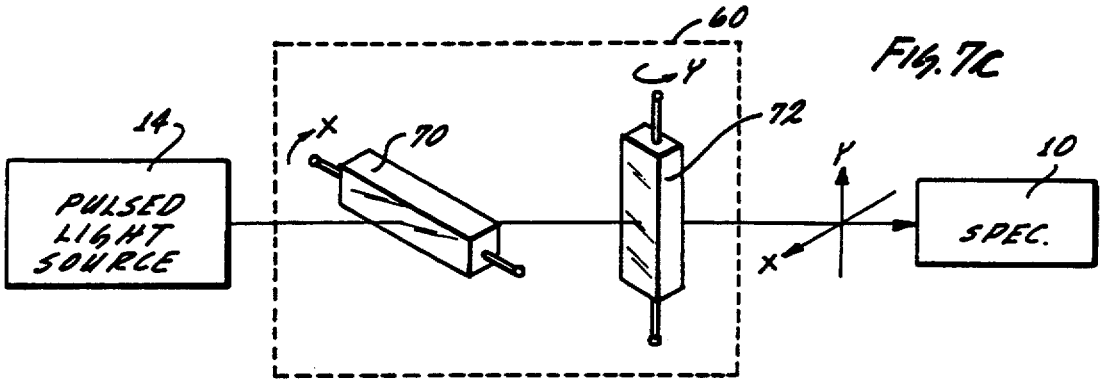

In FIGS. 5 and 6, the information at a plurality of spots on the specimen is detected using two different techniques. FIGS. 7 (a), (b) and (c) illustrate alternative methods of producing this detection of information at a plurality of spots and with these alternate methods incorporated in a structure such as the fluorometer of FIG. 4. Specifically, as shown in FIG. 4 at the position of the dotted block 60, an X-Y positioner may be used to control the exciting light from pulsed light source to excite the specimen 10 at a plurality of spots for detection.

FIG. 7 (a) illustrates a first embodiment of the scanner 60 incorporating a pair of tilting or rotating mirrors 62 and 64 such as galvanometer scanning mirrors each producing one axis of movement of the exciting light from the pulsed light source 14 to produce the X-Y scanning of the specimen 10.

FIG. 7 (b) illustrates a second embodiment of the scanner 60 incorporating an acoustic-optic (AO) modulator 66 and a tilting or rotating mirror 68 each producing one axis of movement of the exciting light from the pulsed light source 14 to produce the X-Y scanning of the specimen 10.

FIG. 7 (c) illustrates a third embodiment of the scanner 60 incorporating a pair of AO modulators 70 and 72, each producing one axis of movement of the exciting light from the pulse of light source 14 to produce the X-Y scanning of the specimen 10.

In these scanning systems, the scanning is accomplished by movement of the beam in the x and in the y directions so as to systemically illuminate in succession each point in a field. If large areas are to be scanned these systems may be combined with the stepping stage to provide movement from field to field. Deflections may be accomplished by the galvanometer scanning mirror which reflects the beam in the desired direction or by the acoustic optics (AO) modulator which deviates the beam into the desired direction.

The position of a galvanometer scanning mirror is controlled by the current flow through a coil in a magnetic field. The deviation of a beam by the AO modulator is a function of the frequency applied to the AO material which then behaves like a diffraction grating. Undeviated light is blanked off optically. In the AO material, standing waves are set up producing a set of bands of refractive index gradients by which the light is deviated. A sonic transducer in contact with the AO material produces the periodic mechanical stress within the AO material.

The electro-optic modulator 26 used in the embodiments of FIGS. 4, 5 and 6 is preferably a modulator of a high numerical aperture to allow the collection and passage of as much light as possible. The use of such an electro-optic modulator provides for an improved signal to noise ratio for the overall system. In general, the electro-optic modulator should have the following characteristics a high speed which thereby implies a large electro-optic coefficient at gigahertz frequencies together with small power consumption to thereby permit reasonable size power supplies; large angular or numerical aperture which is the most important requirement since the numerical aperture of the optical system should not be less than that of a good microscopic objective. The large numerical aperture is therefore desirable to a obtain the needed optical resolution to permit formation of a high quality optical image.

It has been generally known that crystals of the cubic class $T_d$ (or $\bar{4}3$ m) offer the maximum angular aperture for devices based on longitudinal or transverse Pockels effects. The following factors are generally involved in the choice of the particular material to be used in the electro-optic modulator of the present invention. Specifically, when an electric field is applied to a cubic crystal (isotropic) of a class $T_d$ the crystal becomes birefrigent. In general, it becomes biaxial and maximum retardation is obtained for light in 110 direction and field in the 110 direction. If the field is applied in the 111 direction the crystal becomes uniaxial, the 111 direction being the optic axis. A light beam passing in any direction perpendicular to the 111 direction has a retardation $\sqrt{3}/2$ times the maximum retardation mentioned above. The use of the latter (transverse) mode has the advantage that the electrodes on the modulator need not be transparent thereby allowing low resistivity to be easily obtainable. The following group of cubic crystals belong to a group from which the electro-optic modulator of the present invention may be constructed. These cubic crystals include:

CuCl (Cuprous chloride)
CuBr (Cuprous bromide)
CuI (Cuprous iodide)
ZnS (Zinc sulfide)
ZnSe (Zinc selenide)
ZnTe (Zinc telluride)
$(CH_2)_6N_4$ (Hexamine or Hexamethylenetetramine)
$(Na, Ca)_{8-4}(SO_4)_{2-1}[(AlSiO_4)_6]$(Hauynite)
GaP (Gallium phosphide)
$Bi_4(GeO_4)_3$ (Bismuth germanate)
$NaClO_3$ (Sodium chlorate)
$BaTiO_3$ (Barium titanate)
$SrTiO_3$ (Strontium titanate)
$KTaO_3$ (Potassium tantalate)
$KTa_xNb_{1-x}O_3$ (Potassium tantalate niobate)

The use of electro-optic modulators, formed by cubic crystals of the class $T_d$ providing for the time gating, allow for a high quality optical imaging of the fluorescent source from the specimens. These modulators operate with large numerical apertures and are therefore suitable for use in the gated fluorescent microscope of the present invention. The use of these electro-optic modulators makes possible the production of an optical image that can be viewed in a similar way to normal microscopy.

Figure 8:
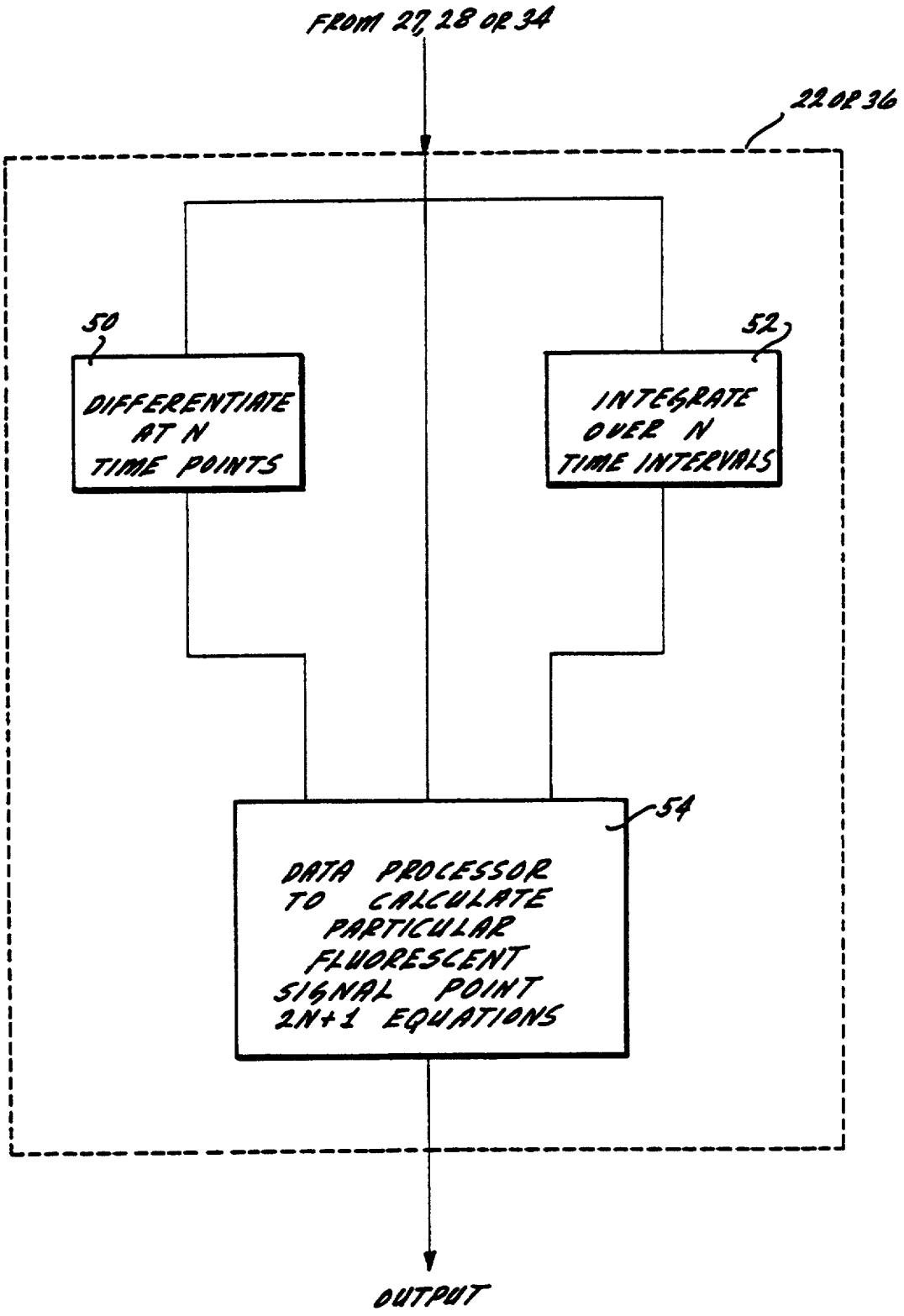
FIG. 8 is a block diagram of a method of analysis of the fluorescent signal.

As disclosed above, these electro-optic modulators may be incorporated in the two embodiments of a fluoromicroscope shown in FIGS. 5 and 6. In addition, the output fluorescent signal may be enhanced using the unique methods of analysis of the fluorescent data to further separate this data from the background fluorescence. Specifically, as shown in FIG. 8 one of the methods extracts a particular desired fluorescent signal having a known decay from a background of unknown noise signals. The method encompasses differentiating the composite signal at a predetermined number of time points as shown in block 50 and integrating the composite signal over a predetermined number of time intervals as shown in block 52. A computer 54 is then used to eliminate the unknowns using the multiple equations formed by the differentiation and integration to thereby extract the intensity of the desired fluorescent decay signal.

The present invention therefore provides for an apparatus and method of producing an improved detection of fluorescent signals and provides for discrimination between the desired fluorescent signal and the background noise.

The present invention provides for excitation by a light pulse very short compared to the decay time of the fluorophore. The light pulse is also of sufficient energy to excite all, or nearly all of the fluorophore molecules in the illuminated sample. The light pulse may be produced by a number of different means. For example, the invention provides for the production of a short, high energy pulse of light by the use of a pulsed laser. In addition, the invention may provide for the short, high energy pulse of light by means of an intense continuous source or wide pulse source in conjunction with an optical shutter. The shutter for example, may be an electro-optic modulator or an AO modulator.

The fluorophore signal contained in the total observed fluorescence may be enhanced, as compared to the background fluorescence, by means of time gating. The time gating may be implemented by a variety of different means. For example, an electronically gated photomultiplier tube or other suitable photodetector may provide the time gating. Other suitable photodetectors may include an electronically gated image tube or an electronically gated photosensitive array. The time gating may also be provided by an optical shutter. For example, a Pockels cell may be used to provide an optical shutter. In addition, other electro-optic modulators may be used to provide a shutter and the invention specifically provides for the use of modulators made from cubic crystals of the class $T_d$ as optical shutters having large numerical apertures.

The various embodiments of the invention may provide for the detection of the fluorophore signal from a variety of different types of detectors. For example, detectors such as photo-multipliers, image tubes or photosensitive arrays may be used to detect the fluorescence of interest. In addition, microscope optics may be used to form an image of the fluorescence sample with such microscope optics forming part of the detector.

Once the fluorescence of interest is detected, the signal may be electronically processed in a variety of different ways. In particular, a photosensitive array may be electronically scanned so as to determine for each pixel the fluorescence intensity averaged over the duration of an arbitrary time window. Another processing technique would be measurement of the fluorescence from a sample so as to determine from each pixel the fluorescence intensity averaged over the duration of an arbitrary time window, or as a function of time over a time window. In the processing, the fluorescence intensity may be digitized with any of the processing techniques. Other aspects of the processing could be the measurement of the fluorescence intensity as a function of time after a single excitation pulse, or the measurement of the time integral of the fluorescence intensity after each of a number of excitation pulses, and with the integration carried out over a different time interval for each pulse.

After the fluorescence of interest has been detected and processed, it may now be analyzed using one of the methods of the present invention. Specifically, the fluorophore signal may be extracted from the total observed fluorescence by means of Hybrid Laplace Transform Amplitude Analysis or by Normalized Background Analysis. In addition, a reconstruction of an image of the fluorescence sample may be produced from the digital data relating to the fluorescence intensity.

Although the invention has been described with reference to particular embodiments, it is to be appreciated that variation adaptations and modifications may be made and the invention is only to be limited to the appended claims.

We claim:

1. A fluorometer for measuring *the fluorescence from a specimen having a background fluorescence and* a particular fluorescence emanating from particular fluorophore molecules in [a] *the* specimen *and for distinguishing the measurements of the particular fluorescence from the measurements of the background fluorescence*, including, means for producing a burst of concentrated light energy having a pulse time short compared to the decay time of the particular fluorescence and having sufficient energy to excite substantially all of the particular fluorophore molecules, means responsive to the burst of concentrated light energy for directing the burst of concentrated light energy toward the specimen to produce a fluorescence from the specimen including the particular fluorescence *and the background fluorescence*, means responsive to the *particular* fluorescence *and the background fluorescence* from the specimen for detecting [the fluorescence] *such fluorescences* and for producing signals in accordance with such detection, means coupled to the detecting means for controlling the detecting means within a particular time period, *after the burst of the concentrated light energy*, to optimize the detection of the particular fluorescence and to enhance the detection of the particular fluorescence relative to the [total] *detection of the background* fluorescence, the beginning of the particular time period being defined by a first particular time after the burst of concentrated light energy and during the production of the particular fluorescence *and the background fluorescence* and the end of the particular time period being defined by a second particular time after the first particular time where the second particular time occurs during the production of the particular fluorescence [from the specimen as a result of the burst of the concentrated light energy], means coupled to the burst producing means, to the detecting means and to the controlling means for timing the operation of [the above] *such* means to sequence the detection of the [fluorescence] *fluorescences* during the particular time period [as a result of] *after* the production of the burst of concentrated light energy, means [coupled to the detection means for forming] *responsive to the signals produced in accordance with*

*the detection during the particular time period for distinguishing the particular fluorescence produced during the particular time period from the background fluorescence produced during the particular time period and for producing output* signals representative *substantially only* of the particular fluorescence from the specimen *during the particular time period*, and means responsive to the [detection of] *output signals representing substantially only* the particular fluorescence from the specimen during the particular time period for producing an image of the particular fluorescence.

2. The fluorometer of claim 1 wherein the means for [forming signals] *detecting the fluorescences* includes means for producing a scanning of the particular [fluorescence] *fluorescences* from the specimen during the particular time period at different positions on the specimen.

3. The fluorometer of claim 2 wherein the means for detecting includes a photosensitive array for detecting the fluorescence emanating from a plurality of spots on the specimen and the means for scanning includes an array control for scanning the photosensitive array to obtain a reproduction of the detected fluorescence of the different spots on the specimen.

4. The fluorometer of claim 2 wherein the means for scanning includes a stepping stage for supporting the specimen and for moving the specimen to a plurality of different positions for providing a detection of the fluorescence emanating from the specimen at the different positions.

5. A fluorometer for measuring *the fluorescence from a specimen having a background fluorescence and* a particular fluorescence emanating from particular fluorophore molecules in [a] *the* specimen *and for distinguishing the measurements of the particular fluorescence from the measurements of the background fluorescence, the particular fluorescence having different characteristics than the background fluorescence*, including means for producing a burst of concentrated light energy having a pulse time short compared to the decay time of the particular fluorescence and having sufficient energy to excite substantially all of the particular fluorophore molecules, means responsive to the concentrated light energy for directing the concentrated light energy toward the specimen to produce [fluorescence] *fluorescences* from the specimen including the particular fluorescence *and the background fluorescence*, means responsive to the *particular* fluorescence *and the background fluorescence from the specimen* for detecting [the fluorescence ] *such fluorescences* and for producing signals in accordance with [the fluorescence] *such detection*, means coupled to the detecting means for controlling the detecting means within a particular time period [to optimize the detection of the particular fluorescence] *after the burst of the concentrated light energy* and wherein the controlling means is an electro-optic modulator formed by a cubic crystal of the class $T_d$, *the fluorescence produced during the particular time period including the particular fluorescence and the background fluorescence*, means coupled to the burst producing means, to the detecting means and to the controlling means for timing the operation of the above means to sequence the detection of the fluorescence within the particular time period after the production of the burst of concentrated light energy, and data processing means responsive to the signals produced by the detecting means for [analysing the signals to enhance] *distinguishing* the portion of the signals [representing] *produced during the particular time period in representation of* the particular fluorescence [relative to] *from* the portion of the signals [representing the remaining] *produced during the particular time period in representation of the background* fluorescence *and for processing substantially only the portion of the signals representing the particular fluorescence to measure the particular fluorescence.*

6. The fluorometer of claim 5 additionally including means for producing a scanning of the [fluorescence] *fluorescences* from the specimen for forming signals representative of the [fluorescence] *fluorescences* from the specimen.

7. The fluorometer of claim 6 wherein the means for detecting includes a photosensitive array for detecting the fluorescence emanating from a plurality of spots on the specimen and the means for scanning includes an array control for scanning the photosensitive array to reproduce the detected fluorescence of the different spots on the specimen.

8. The fluorometer of claim 6 wherein the means for scanning includes a stepping stage for supporting the specimen and for moving the specimen to a plurality of different positions for providing a detection of the fluorescence emanating from the specimen at the different positions.

9. The fluorometer of claim 5 additionally including means responsive *substantially only* to the *signals representing the particular* fluorescence from the specimen for producing an image of [the] *such* fluorescence [and with the controlling means controlling the detecting means within a particular time period by detector responsive means] and *the detecting means* additionally including means for forming signals including [a] means for producing a scanning of the fluorescence from the specimen.

10. The fluorometer of claim 9 wherein the means for detecting includes a photosensitive array for detecting the fluorescence emanating from a plurality of spots on the specimen and the means for scanning includes an array control for scanning the photosensitive array to reproduce the detected fluorescence of the different spots on the specimen.

11. The fluorometer of claim 9 wherein the means for scanning includes a stepping stage for supporting the specimen and for moving the specimen to a plurality of different positions for providing a detection of the fluorescence emanating from the specimen at the different positions.

12. The fluorometer of claim 5 additionally including means responsive to the fluorescence from the specimen for producing an image of the fluorescence and with the controlling means controlling the passage of the image of the fluorescence to the detecting means and additionally including means for forming signals including means for observing or recording of the fluorescence from the specimen.

13. The fluorometer of claim 12 wherein the means for detecting includes a photodetector for detecting the [fluorescence] *fluorescences* emanating from the specimen.

14. The fluorometer of claim 12 wherein the means for detecting includes an image tube to reproduce the pattern of [fluorescence] *fluorescences* emanating from a plurality of spots on the specimen.

15. The fluorometer of claim 12 wherein the means for detecting includes [the] *a* camera to analyze or record the [fluorescence] *fluorescences* emanating from a plurality of spots on the specimen.

16. The fluorometer of claim 5 additionally including means responsive to the [fluorescence] *fluorescences* from the specimen for producing an image of the [fluorescence] *fluorescences* and [with the controlling means controlling the detecting means within a particular time period by detector responsive means and] additionally including means for forming signals including means for observing or recording *substantially only* the *particular* fluorescence from the specimen.

17. The fluorometer of claim 16 wherein the means for detecting includes a photodetector for detecting the [fluorescence] *fluorescences* emanating from the specimen.

18. The fluorometer of claim 16 wherein the means for detecting includes an image tube to reproduce the pattern of [fluorescence] *fluorescences* emanating from a plurality of spots on the specimen.

19. The fluorometer of claim 5 wherein the means for producing the burst of concentrated light energy is a laser.

20. The fluorometer of claim 5 wherein the means for producing the burst of concentrated light energy is a continuous wave source directing light energy through a modulator.

21. The fluorometer of claim 20 wherein the cubic crystal of the class $T_d$ is cuprous chloride.

22. The fluorometer of claim 20 wherein the electro-optic modulator is formed from at least one of the following group of materials:

CuCl (Cuprous chloride)
CuBr (Cuprous bromide)
CuI (Cuprous iodide)
ZnS (Zinc sulfide)
ZnSe (Zinc selenide)
ZnTe (Zinc telluride)
$(CH_2)_6N_4$(Hexamine or Hexamethylenetetramine)
$(Na, Ca)_{8-4}(SO_4)_{2-1}[(AlSiO_4)_6]$ (Hauynite)
GaP (Gallium phosphide)
$Bi_4(GeO_4)_3$ (Bismuth germanate)
$NaClO_3$ (Sodium chlorate)
$BaTiO_3$ (Barium titanate)
$SrTiO_3$ (Strontium titanate)
$KTaO_3$ (Potassium tantalate)
$KTa_xNb_{1-x}O_3$ (Potassium tantalate niobate)

23. The fluorometer of claim 5 wherein the time period [is relatively long and] has an ending time sufficiently long to have substantially all of the [fluorescence] *fluorescences* decayed *at the end of such time period* to a low value relative to the original value of [fluorescence] *such fluorescences*.

24. A fluorometer for measuring *the fluorescence from a specimen having a background fluorescence and* a particular fluorescence emanating from particular fluorophore molecules in [a] *the* specimen *and for distinguishing the measurements of the particular fluorescence from the measurements of the background fluorescence*, including means for producing a burst of concentrated light energy having a pulse time short compared to the decay time of the particular fluorescence and having sufficient energy to excite substantially all of the particular fluorophore molecules, means responsive to the concentrated light energy for directing the concentrated light energy toward the specimen to produce a fluorescence from the specimen including the particular fluorescence *and the background fluorescence,* means responsive to the *particular* fluorescence *and the background fluorescence* for detecting [the fluorescence] *such fluorescences* and for producing signals in accordance with [the fluorescence] *such detection,* means coupled to the detecting means for controlling the detecting means within a particular time period *after the burst of the concentrated light energy* to optimize the detection of the particular fluorescence and wherein the controlling means is an electro-optic modulator formed by a cubic crystal of the class $T_d$, *the particular fluorescence and the background fluorescence occurring during the particular time period,*

*the particular fluorescence and the background fluorescence having individual decays and the decay of the particular fluorescence being different from the decay of the background fluorescence,* means coupled to the burst producing means, to the detecting means and to the controlling means for timing the operation of the above means to sequence the detection of the fluorescence within the particular time period after the production of the burst of concentrated light energy, and means coupled to the [detection] *detecting* means for [forming signals representative of the particular fluorescence from the specimen] *distinguishing the decay of the particular fluorescence during the particular time period from the decay of the background fluorescence during the particular time period and for thereby determining the characteristics substantially only of the particular fluorescence in the specimen.*

25. The fluorometer of claim 24 wherein the cubic crystal of the class $T_d$ is cuprous chloride.

26. The fluorometer of claim 24 additionally including means responsive to the fluorescence from the specimen for producing an image of the fluorescence and with the controlling means controlling the passage of the image of the fluorescence to the detecting means and with the means for forming signals including a means for producing a scanning of the fluorescence from the specimen.

27. The fluorometer of claim 26 wherein the means for detecting includes a photosensitive array for detecting the [fluorescence] *fluorescences* emanating from a plurality of spots on the specimen and the means for scanning includes an array control for scanning the photosensitive array to reproduce the detected [fluorescence] *fluorescences* of the different spots on the specimen.

28. The fluorometer of claim 26 wherein the means for scanning includes a stepping stage for supporting the specimen and for moving the specimen to a plurality of different positions for providing a detection of the [fluorescence] *fluorescences* emanating from the specimen at the different positions.

29. The fluorometer of claim 24 additionally including means responsive to the [fluorescence] *fluorescences* from the specimen for producing an image of the [fluorescence and the controlling means including detector responsive means for controlling the detecting means within a particular time period] *fluorescences* and the means for [forming] *producing* signals including means for producing a scanning of the [fluorescence] *fluorescences* from the specimen.

30. The fluorometer of claim 29 wherein the means for detecting includes a photosensitive array for detecting the [fluorescence] *fluorescences* emanating from a plurality of spots on the specimen and the means for scanning includes an array control for scanning the photosensitive array to reproduce the detected [fluorescence] *fluorescences* of the different spots on the specimen.

31. The fluorometer of claim 29 wherein the means for scanning includes a stepping stage for supporting the specimen and for moving the specimen to a plurality of different positions for providing a detection of the [fluorescence] *fluorescences* emanating from the specimen at the different positions.

32. The fluorometer of claim 24 additionally including means responsive to the [fluorescence] *fluorescences* from the specimen for producing an image of the [fluorescence] *fluorescences* and with the controlling means controlling the passage of the image of the [fluorescence] *fluorescences* to the detecting means and with the means for forming signals including means for observing or recording [of] the [fluorescence] *fluorescences* from the specimen.

33. The fluorometer of claim 32 wherein the means for detecting includes a photodetector for detecting the [fluorescence] *fluorescences* emanating from the specimen.

34. The fluorometer of claim 32 wherein the means for detecting includes an image tube to reproduce the pattern of [fluorescence] *fluorescences* emanating from a plurality of spots on the specimen.

35. The fluorometer of claim 32 wherein the means for detecting includes a camera to analyze or record the [fluorescence] *fluorescences* emanating from a plurality of spots on the specimen.

36. The fluorometer of claim 24 additionally including means responsive to the [fluorescence] *fluorescences* from the specimen for producing an image of the [fluorescence and with the controlling means controlling the detecting means within a particular time period by detector responsive means] *fluorescences* and with the means for forming signals including means for observing or recording of the [fluorescence] *fluorescences* from the specimen.

37. The fluorometer of claim 36 wherein the means for detecting includes a photodetector for detecting the [fluorescence] *fluorescences* emanating from the specimen.

38. The fluorometer of claim 36 wherein the means for detecting includes an image tube to reproduce the pattern of [fluorescence] *fluorescences* emanating from a plurality of spots on the specimen.

39. The fluorometer of claim 24 wherein the means for producing the burst of concentrated light energy is a laser.

40. The fluorometer of claim 24 wherein the means for producing the burst of concentrated light energy is a continuous wave source directing light energy through a modulator.

41. The fluorometer of claim 24 wherein the *particular* time period has a beginning time and an ending time defining a sufficiently short time to enhance the detection of the particular fluorescence relative to the [total] *background* fluorescence.

42. The fluorometer of claim 24 additionally including data processing means responsive to the signals produced by the detecting means for analysing the signals to enhance the portion of the signals representing the particular fluorescence relative to the portion of the signals representing the [remaining] *background* fluorescence.

43. The fluorometer of claim 42 wherein the time period [is relatively long and] has an ending time sufficiently long to have substantially all of the [fluorescence] *fluorescences* decayed to a low value relative to the original value of [fluorescence] *fluorescences.*

44. A fluorometer for measuring *the fluorescence from a specimen having a background fluorescence and* a particular fluorescence emanating from particular fluorophore molecules in [a] *the* specimen *and for distinguishing the measurements of the particular fluorescence from the measurements of the background fluorescence,* including means for producing a burst of concentrated light energy having a pulse time short compared to the decay time of the particular fluorescence and having sufficient energy to excite substantially all of the particular fluorophore molecules, means responsive to the concentrated light energy for directing the concentrated light energy toward the specimen to produce [a fluorescence] *fluorescences* from the specimen including the particular fluorescence *and the background fluorescence,* means responsive to the *particular* fluorescence *and the background fluorescence* for detecting the [fluorescence] *fluorescences* and for [producing] *analyzing the detected fluorescences as a function of time to produce* signals [in accordance with the fluorescence] *distinguishing the particular fluorescence from the background fluorescence and representing substantially only the particular fluorescence,* means coupled to the detecting means for controlling the detecting means within a particular time period, *after the burst of the concentrated light energy,* to optimize the [detection of] *analysis to distinguish* the particular fluorescence *from the background fluorescence* and wherein the controlling means is an electro-optic modulator formed from at least one of the following group of materials:

CuCl (Cuprous chloride)
CuBr (Cuprous bromide)
CuI (Cuprous iodine)
ZnS (Zinc sulfide)
ZnSe (Zinc selenide)
ZnTe (Zinc telluride)
$(CH_2)_6N_4$ (Hexamine or hexamethylenetetramine)
$(Na, Ca)_{8-4}(SO_4)_{2-1}[(AlSiO_4)_6]$(Hauynite)
GaP (Gallium phosphide)
$Bi_4(GeO_4)_3$ (Bismuth germanate)
$NaClO_3$ (Sodium chlorate)
$BaTiO_3$ (Barium titanate)
$SrTiO_3$ (Strontium titanate)
$KTaO_3$ (Potassium tantalate)
$KTa_xNb_{1-x}O_3$ (Potassium tantalate niobate)

45. A fluorometer for measuring *the fluorescence from a specimen having a background fluorescence and* a particular fluorescence emanating from particular fluorophore molecules in [a] *the* specimen *and for distinguishing the measurements of the particular fluorescence*

*from the measurements of the background fluorescence,* including means for producing a burst of concentrated light energy having a pulse time short compared to the decay time of the particular fluorescence and having sufficient energy to excite substantially all of the particular fluorophore molecules, means responsive to the concentrated light energy for directing the concentrated light energy toward the specimen to produce [a fluorescence] *fluorescences* from the specimen including the particular fluorescence *and the background fluorescence,* means responsive to the *particular* fluorescence *and the background fluorescence from the specimen* for detecting [the fluorescence] *such fluorescences* and for producing signals in accordance with [the fluorescence] *such detection,* means coupled to the detecting means for controlling the detecting means within a particular time period, *after the burst of the concentrated light energy,* to optimize the detection of the particular fluorescence *relative to the background fluorescence,* means coupled to the burst producing means, to the detecting means and to the controlling means for timing the operation of the above means to sequence the detection of the *produced* fluorescence within the particular time period after the production of the burst of concentrated light energy, and means coupled to the [detection] *detecting* means for forming signals representative of the particular fluorescence *and the background fluorescence* from the specimen, and data processing means responsive to the signals produced by the [detecting] *signal-forming* means *during the particular time period* for [analysing the signals to enhance] *enhancing* the portion of the signals representing the particular fluorescence relative to the portion of the signals representing the [remaining] *background* fluorescence, and wherein the data processing means includes first means for differentiating the signals produced by the detecting means at a number of time points *during the particular time period* to produce a plurality of individual time point signals, second means for integrating the signals produced by the detecting means over a [corresponding] number of time intervals *during the particular time period* to produce a plurality of individual time integrated signals and third means responsive to the signals from the [detecting] *signal-forming* means, the individual time point signals and the individual time integrated signals *during the particular time period* for operating upon these signals in a particular relationship to *distinguish the particular fluorescence from the background fluorescence and to* determine *substantially only* the particular fluorescence from the specimen during the particular *time* period as a result of the burst of concentrated light energy.

46. The fluorometer of claim 45 additionally including means responsive to the [fluorescence] *fluorescences* from the specimen for producing an image of the [fluorescence] *fluorescences* and with the controlling means controlling the passage of the image of the [fluorescence] *fluorescences* to the detecting means and with the means for forming signals including a means for producing a scanning of the [fluorescence] *fluorescences* from the specimen.

47. The fluorometer of claim 46 wherein the means for detecting includes a photosensitive array for detecting the [fluorescence] *fluorescences* emanating from a plurality of spots on the specimen and the means for scanning includes an array control for scanning the photosensitive array to reproduce the detected [fluorescence] *fluorescences* of the different spots on the specimen.

48. The fluorometer of claim 46 wherein the means for scanning includes a stepping stage for supporting the specimen and for moving the specimen to a plurality of different positions for providing a detection of the [fluorescence] *fluorescences* emanating from the specimen at the different position.

49. The fluorometer of claim 45 additionally including means responsive to the [fluorescence] *fluorescences* from the specimen for producing an image of [the fluorescence and the controlling means including detector responsive means for controlling the detecting means within a particular time period] *such fluorescences* and the means for forming signals including means for producing a scanning of the [fluorescence] *fluorescences* from the specimen.

50. The fluorometer of claim 49 wherein the means for detecting includes a photosensitive array for detecting the [fluorescence] *fluorescences* emanating from a plurality of spots on the specimen and the means for scanning includes an array control for scanning the photosensitive array to reproduce the detected [fluorescence] *fluorescences* of the different spots on the specimen.

51. The fluorometer of claim 49 wherein the means for scanning includes a stepping stage for supporting the specimen and for moving the specimen to a plurality of different positions for providing a detection of the [fluorescence] *fluorescences* emanating from the specimen at the different positions.

52. The fluorometer of claim 45 additionally including means responsive to the [fluorescence] *fluorescences* from the specimen for producing an image of the [fluorescence] *fluorescences* and with the controlling means controlling the passage of the image of the [fluorescence] *fluorescences* to the detecting means and with the means for forming signals including means for observing or recording of the [fluorescence] *fluorescences* from the specimen.

53. The fluorometer of claim 52 wherein the means for detecting includes a photodetector for detecting the [fluorescence] *fluorescences* emanating from the specimen.

54. The fluorometer of claim 52 wherein the means for detecting includes an image tube to reproduce the pattern of fluorescence emanating from a plurality of spots on the specimen.

55. The fluorometer of claim 52 wherein the means for detecting includes a camera to analyze or record the fluorescence emanating from a plurality of spots on the specimen.

56. The fluorometer of claim 45 additionally including means responsive to the [fluorescence] *fluorescences* from the specimen for producing an image of the [fluorescence and with the controlling means controlling the detecting means within a particular time period by detector responsive means] *fluorescences* and with the means for forming signals including means for observing or recording [of] the [fluorescence] *fluorescences* from the specimen.

57. The fluorometer of claim 56 wherein the means for detecting includes a photodetector for detecting the [fluorescence] *fluorescences* emanating from the specimen.

58. The fluorometer to claim 56 wherein the means for detecting includes an image tube to reproduce the pattern of [fluorescence] *fluorescences* emanating from a plurality of spots on the specimen.

59. The fluorometer of claim 45 wherein the means for producing the burst of concentrated light energy is a laser.

60. The fluorometer of claim 45 wherein the means for producing the burst of concentrated light energy is a continuous wave source directing light energy through a modulator.

61. The fluorometer of claim 45 wherein the means for controlling the detecting means within a particular time period is an electro-optic modulator.

62. The fluorometer of claim 45 wherein the *particular* time period has a beginning time and an ending time defining a sufficiently short time to enhance the detection of the particular fluorescence relative to the [total ] *detection of the background* fluorescence.

63. The fluorometer of claim 45 wherein the *particular* time period [is relatively long and] has an ending time sufficiently long to have substantially all of the fluorescence decayed to a low value relative to the original value of fluorescence.

64. A fluorometer for measuring *the fluorescence from a specimen having a background fluorescence and* a particular fluorescence emanating from particular fluorophore molecules in [a] *the* specimen *and for distinguishing the measurement of the particular fluorescence from the measurement of the background fluorescence,* including, means for producing a burst of concentrated light energy having a pulse time short compared to the decay time of the particular fluorescence and having sufficient energy to excite substantially all of the particular fluorophore molecules, means responsive to the burst of concentrated light energy for directing the burst of concentrated light energy toward the specimen to produce a fluorescence from the specimen including the particular fluorescence *and the background fluorescence,* means responsive to the *particular* fluorescence *and the background fluorescence* from the specimen for detecting [the fluorescence] *such fluorescences* and for producing signals in accordance with such detection, means coupled to the detecting means for obtaining a controlled operation of the detecting means during a particular time period *after the burst of the concentrated light energy* to optimize the detection of the particular fluorescence and wherein the *particular* time period has a beginning time and an ending time to enhance the detection of the *portion of the* signals representing the particular fluorescence relative to the portion of the signals representing the [remaining] *background* fluorescence, the beginning time of the particular time period being a first particular time after the burst of *the* concentrated light energy and after the production of the particular fluorescence *and the background fluorescence*, and the ending time being a second particular time after the first particular time and during the production of the particular fluorescence from the specimen as a result of the burst of concentrated light energy, means coupled to the burst producing means, to the detecting means and to the controlling means for timing the operation of the detecting means to sequence the detection of the *particular* fluorescence during the particular time period as a result of the production of the burst of concentrated light energy, and data processing means responsive to the signals produced by the detecting means during the particular time period for [analysing the signals to enhance] *distinguishing* the portion of the signals representing the particular fluorescence during the particular time [interval relative to] *period from* the portion of the signals representing the [remaining] *background* fluorescence during the particular time [interval] *period and for producing signals representing substantially only the particular fluorescence.*

65. A fluorometer as set forth in claim 64 wherein the detecting means includes means for scanning the [fluorescence] *fluorescences* from the specimen to obtain the production of the signals representative of the [fluorescence] *fluorescences* from the specimen as a result of the production of the burst of concentrated light energy.

66. The fluorometer of claim 65 wherein the means for detecting includes a photosensitive array for detecting the [fluorescence] *fluorescences* emanating from a plurality of spots on the specimen and the means for scanning includes an array control for scanning the photosensitive array to reproduce the detected [fluorescence] *fluorescences* of the different spots on the specimen.

67. The fluorometer of claim 65 wherein the means for scanning includes a stepping stage for supporting the specimen and for moving the specimen to a plurality of different positions for providing a detection of the [fluorescence] *fluorescences* emanating from the specimen at the different positions.

68. A fluorometer for measuring *the fluorescence from a specimen having a background fluorescence and* a particular fluorescence emanating from particular fluorophore molecules in [a] *the* specimen *and for distinguishing the measurements of the particular fluorescence from the measurements of the background fluorescence,* including means for producing a burst of concentrated light energy having a pulse time short compared to the decay time of the particular fluorescence and having sufficient energy to excite substantially all of the particular fluorophore molecules, means responsive to the concentrated light energy for directing the concentrated light energy toward the specimen to produce [fluorescence] *fluorescences* from the specimen including the particular fluorescence *and the background fluorescence,* means responsive to the *particular* fluorescence *and the background fluorescence from the specimen* for detecting [the fluorescence] *such fluorescences* and for producing signals in accordance with [the fluorescence] *such detection,* means coupled to the detecting means for controlling the detecting means within a particular time period, *after the burst of the concentrated light energy,* to optimize the detection of the particular fluorescence, means coupled to the burst producing means, to the detecting means and to the controlling means for timing the operation of the above means to sequence the detection of the *particular* fluorescence *and the background fluorescence from the specimen* within the particular time period after the production of the burst of *the* concentrated light energy, *and* data processing means responsive to the signals produced by the detecting means *during the particular time period* for [analysing the signals to enhance] *enhancing* the portion of the signals representing the particular fluorescence *during the particular time period* relative to the portion of the signals representing the [remaining] *background* fluorescence *during the particular time period*, and the data processing means including first means for differentiating the signals produced by the detecting means at a number of time points *during the particular time period* to produce a plurality of individual time point signals, second means for integrating the signals produced by the detecting means over a [corresponding] number of time intervals *during the particular time period* to produce a plurality of individual time integrated signals and third means responsive to the signals from the detecting means, the individual time point signals and the individual time integrated signals *during the particular time period* for producing signals representing *substantially only* the particular fluorescence.

69. The fluorometer of claim 68 additionally including means for producing a scanning of the [fluorescence] *fluorescences* from the specimen for forming signals representative of the [fluorescence] *fluorescences* from the specimen.

70. The fluorometer of claim 69 wherein the means for detecting includes a photosensitive array for detecting the [fluorescence] *fluorescences* emanating from a plurality of spots on the specimen and the means for scanning includes an array control for scanning the photosensitive array to reproduce the detected [fluorescence] *fluorescences* of the different spots on the specimen.

71. The fluorometer of claim 69 wherein the means for scanning includes a stepping stage for supporting the specimen and for moving the specimen to a plurality of different positions for providing a detection of the [fluorescence] *fluorescences* emanating from the specimen at the different positions.

72. The fluorometer of claim 69 additionally including means responsive to the [fluorescence] *fluorescences* from the specimen for producing an image of the [fluorescence and the controlling means including detector responsive means for controlling the detecting means within a particular time period] *fluorescences.*

73. The fluorometer of claim 72 wherein the means for detecting includes a photosensitive array for detecting the [fluorescence] *fluorescences* emanating from a plurality of spots on the specimen and the means for scanning includes an array control for scanning the photosensitive array to reproduce the detected [fluorescence] *fluorescences* of the different spots on the specimen.

74. The fluorometer of claim 72 wherein the means for scanning includes a stepping stage for supporting the specimen and for moving the specimen to a plurality of different positions for providing a detection of the [fluorescence] *fluorescences* emanating from the specimen at the different positions.

75. The fluorometer of claim 68 additionally including means responsive to the [fluorescence] *fluorescences* from the specimen for producing an image of the [fluorescence] *fluorescences* and with the controlling means controlling the passage of the image of the [fluorescence] *fluorescences* to the detecting means and additionally including means for forming signals including means for observing or recording [of] the [fluorescence] *fluorescences* from the specimen.

76. The fluorometer of claim 75 wherein the means for detecting includes a photodetector for detecting the [fluorescence] *fluorescences* from the specimen.

77. The fluorometer of claim 75 wherein the means for detecting includes an image tube to reproduce the pattern of [fluorescence] *fluorescences* emanating from a plurality of spots on the specimen.

78. The fluorometer of claim 75 wherein the means for detecting includes [the human eye or] a camera to analyze or record the [fluorescence] *fluorescences* emanating from a plurality of spots on the specimen.

79. The fluorometer of claim 68 additionally including means responsive to the [fluorescence] *fluorescences* from the specimen for producing an image of the [fluorescence and with the controlling means controlling the detecting means with a particular time period by detector responsive means] *fluorescences* and additionally including means for forming signals including means for observing or recording [of] the [fluorescence] *fluorescences* from the specimen.

80. The fluorometer of claim 79 wherein the means for detecting includes a photodetector for detecting the [fluorescence] *fluorescences* emanating from the specimen.

81. The fluorometer of claim 79 wherein the means for detecting includes an image tube to reproduce the pattern of [fluorescence] *fluorescences* emanating from a plurality of spots on the specimen.

82. The fluorometer of claim 68 wherein the means for producing the burst of concentrated light energy is a laser.

83. The fluorometer of claim 68 wherein the means for producing the burst of concentrated light energy is a continuous wave source directing light energy through a modulator.

84. The fluorometer of claim 68 wherein the means for controlling the passage of the image is an electro-optic modulator.

85. The fluorometer of claim 84 wherein the electro-optic modulator is formed by a cubic crystal of the class $T_d$.

86. The fluorometer of claim 85 wherein the cubic crystal of the class $T_d$ is cuprous chloride.

87. The fluorometer of claim 85 wherein the electro-optic modulator is formed from at least one of the following group of materials:

CuCl (Cuprous chloride)
CuBr (Cuprous bromide)
CuI (Cuprous iodide)
ZnS (Zinc sulfide)
ZnSe (Zinc selenide)
ZnTe (Zinc telluride)
$(CH_2)_6N_4$(Hexamine or Hexamethylenetetramine)
$(Na, Ca)_{8-4}(SO_4)_{2-1}[(AlSiO_4)_6]$ (Hauynite)
GaP (Gallium phosphide)
$Bi_4(GeO_4)_3$ (Bismuth germanate)
$NaClO_3$ (Sodium chlorate)
$BaTiO_3$ (Barium titanate)
$SrTiO_3$ (Strontium titanate)

$KTaO_3$ (Potassium tantalate) $KTa_xNb_{1-x}O_3$ (Potassium tantalate niobate)

88. The fluorometer of claim 68 wherein the *particular* time period [is relatively long and] has an ending time sufficiently long to have substantially all of the [fluorescence] *fluorescences* decayed to a low value relative to the original value of [fluorescence] *fluorescences.*

89. The fluorometer of claim 68 wherein the *particular* time period has a beginning time and an ending time defining a sufficiently short time to enhance the detection of the signals representing the particular fluorescence relative to the portion of the signals representing the [remaining] *background* fluorescence.

90. The fluorometer of claim 68 wherein the *particular fluorescence has a characteristic decay time and* first means produces the plurality of individual time point signals [produces the plurality of individual time point signals] for a specimen not carrying a fluorescent label, said specimen being not necessarily of the same size and disposition as that of the specimen carrying the fluorescent label but consisting of the same material but without *the* added fluorescent label, and the third means extracts from the individual time point signals and the derivatives at the corresponding time points and the characteristics decay time of the particular [fluorescence] *fluorescences* the emission intensity representing the particular fluorescence only and being separated from the background emission.

91. A fluorometer for measuring *the fluorescence from a specimen having a background fluorescence and* a particular fluorescence emanating from particular fluorophore molecules in [a] *the* specimen *and for distinguishing between the measurement of the particular fluorescence and the measurement of the background fluorescence*, including

*the particular fluorescence having a different decay time than the background fluorescence,* means for producing a burst of concentrated light energy having a pulse time short compared to the decay time of the particular fluorescence and having sufficient energy to excite substantially all of the particular fluorophore molecules, means responsive to the burst of concentrated light energy for directing the burst of concentrated light energy toward the specimen to produce a fluorescence from the specimen including the particular fluorescence *and the background fluorescence,* means responsive to the *particular* fluorescence *and the background fluorescence* from the specimen for detecting [the fluorescence] *such fluorescences* and for producing signals in accordance with such detection, means coupled to the detecting means for obtaining a controlled operation of the detecting means in a particular time period to optimize the detection of the particular fluorescence wherein the *particular* time period has a beginning time and an ending time to enhance the detection of the particular fluorescence relative to the [total] *background* fluorescence, the beginning time occurring a first particular time after the burst of concentrated light energy and during the production of the particular fluorescence *and the background fluorescence* and the ending time occurring a second particular time after the first particular time and during the production of the particular fluorescence *and the background fluorescence* from the specimen as a result of the burst of concentrated light energy, means coupled to the burst producing means, to the detecting means and to the controlling means for timing the operation of the detecting means to sequence the detection of the fluorescence during the particular time period as a result of the production of the burst of concentrated light energy, *and* means coupled to the detecting means for *distinguishing the particular decay time of the particular fluorescence during the particular time period from the decay time of the background fluorescence during the particular time period and for* forming signals representative *substantially only* of the particular fluorescence from the specimen, and means responsive to the [detection of] *signals representing substantially only* the particular fluorescence from the specimen during the particular time period for producing an image of *substantially only* the particular fluorescence during the particular time interval.

92. The fluorometer of claim 71 wherein the means for detecting includes a photosensitive array for detecting the [fluorescence] *fluorescences* emanating from a plurality of spots on the specimen and the means for producing signals includes an array control for scanning the photosensitive array to obtain a reproduction of the detected [fluorescence] *fluorescences* of the different spots on the specimen.

93. The fluorometer of claim 91 including, a stepping stage for supporting the specimen and for moving the specimen to a plurality of different positions for providing a detection of the [fluorescence] *fluorescences* emanating from the specimen at the different positions.

94. A fluorometer for measuring the *the fluorescence from a specimen having a background fluorescence and* a particular fluorescence emanating from particular fluorophore molecules in [a] *the* specimen *and for distinguishing the measurement of the particular fluorescence from the measurement of the background fluorescence*, including means for producing a burst of concentrated light energy having a pulse time short compared to the decay time of the particular fluorescence and having sufficient energy to excite substantially all of the particular fluorophore molecules, means responsive to the burst of concentrated light energy for directing the burst of concentrated light energy toward the specimen to produce a fluorescence from the specimen including the particular fluorescence *and the background fluorescence,* means responsive to the *particular* fluorescence *and the background fluorescence* from the specimen for detecting [the fluorescence] *such fluorescences* and for producing signals in accordance with such detection, means coupled to the detecting means for obtaining a controlled operation of the detecting means during a particular time period, *after the burst of the concentrated light energy,* to optimize the detection of the particular fluorescence wherein the particular time period has a beginning time and an ending time to enhance the detection of the particular fluorescence relative to the [total] *background* fluorescence, the beginning time and the ending time occurring during the production of the particular fluorescence *and the background fluorescence* from the specimen [as a result of] *after* the burst of concentrated light energy, means coupled to the burst producing means, to the detecting means and to the controlling means for timing the operation of the detecting means to sequence the detection of the particular fluorescence *and the background fluorescence* during the particular time period as a result of the production of the burst of concentrated light energy, means coupled to the detecting means for *distinguishing the signals representing the particular fluorescence during the particular time period from the signals representing the background fluorescence during the particular time period and for* forming signals representative *substantially only* of the particular fluorescence from the specimen during the particular time period, means responsive to the *signals representing substantially only the particular* fluorescence from the specimen for producing an image of *substantially only* the particular fluorescence during the particular time period.

95. The fluorometer of claim 94 wherein the means for detecting includes a photodetector for detecting the [fluorescence] *fluorescences* emanating from the specimen.

96. The fluorometer of claim 94 wherein the means for detecting includes an image tube to reproduce the pattern of [fluorescence] *fluorescences* emanating from a plurality of spots on the specimen.

97. The fluorometer of claim 94 wherein the means for detecting includes the camera to analyze or record the [fluorescence] *fluorescences* emanating from a plurality of spots on the specimen.

98. The fluorometer of claim 94 wherein the means for producing the burst of concentrated light energy is a continuous wave source directing light energy through a modulator.

99. The fluorometer of claim 94 wherein the means for controlling the detecting means within a particular time period is an electro-optic modulator.

100. A fluorometer for measuring *the fluorescence from a specimen having a background fluorescence and* a particular fluorescence emanating from particular fluorophore molecules in [a] *the* specimen *and for distinguishing the measurement of the particular fluorescence from the measurement of the background fluorescence*, including means for producing a burst of concentrated light energy having a pulse time short compared to the decay time of the particular fluorescence and having sufficient energy to excite substantially all of the particular fluorophore molecules, means responsive to the burst of concentrated light energy for directing the burst of concentrated light energy toward the specimen to produce [a fluorescence] *fluorescences* from the specimen including the particular fluorescence *and the background fluorescence,* means responsive to the *particular* fluorescence *and the background fluorescence* from the specimen for detecting [the fluorescence] *such fluorescences* and for producing signals in accordance with such detection, means coupled to the detecting means for obtaining a controlled operation of the detecting means during a particular time period, *after the burst of the concentrated light energy,* to optimize the detection of the particular fluorescence during the particular time period, the particular time period having a beginning time and an ending time to enhance the detection of the particular fluorescence relative to the *background* fluorescence [including the particular flourescence], the beginning time and ending time occurring during the production of the particular fluorescence *and the background fluorescence* from the specimen as a result of the production of the burst of concentrated energy, means coupled to the burst producing means, to the detecting means and to the controlling means for timing the operation of the detecting means to sequence the detection of the fluorescence during the particular time period as a result of the production of the burst of concentrated light energy,

*data processing* means coupled to the detecting means for [forming] *differentiating the detected fluorescence, and integrating the detected fluorescence, at progressive instants of time and for processing the results of such differentiation and integration to form* signals representative *substantially only* of the particular fluorescence from the specimen, and means responsive to the signals from the [detecting] *data processing* means during the particular time period *in representation of substantially only the particular fluorescence from the specimen* for producing an image of *substantially only* the particular fluorescence during the particular time period.

101. The fluorometer of claim 100 wherein the means for detecting includes a photodetector for detecting the [fluorescence] *fluorescences* emanating from the specimen.

102. The fluorometer of claim 100 wherein the means for detecting includes an image tube to reproduce the pattern of [fluorescence] *fluorescences* emanating from a plurality of spots on the specimen.

103. The fluorometer of claim 100 wherein the means for producing the burst of concentrated light energy is a laser.

104. The fluorometer of claim 100 additionally including data processing means responsive to the signals produced by the detecting means for analysing the signals to enhance the portion of the signals representing the particular fluorescence relative to the portion of the signals representing the [remaining] *background* fluorescence.

105. A fluorometer as set forth in claim 100, including, means for recording the particular fluorescence from the specimen during the particular time period as a result of the burst of concentrated light energy.

106. A fluorometer for measuring *the fluorescence from a specimen having a background fluorescence and* a particular fluorescence emanating from particular fluorophore molecules in a specimen *and for distinguishing the measurement of the particular fluorescence from the measurement of the background fluorescence*, including means for producing a burst of concentrated light energy having a pulse time short compared to the decay time of the particular fluorescence and having sufficient energy of excite substantially all of the particular fluorophore molecules, means responsive to the burst of concentrated light energy for directing the burst of concentrated light energy toward the specimen to produce a fluorescence from the specimen including the particular fluorescence, means responsive to the *particular* fluorescence *and the background fluorescence* from the specimen for detecting [the fluorescence] *such fluorescences* and for producing signals in accordance with such detection, means coupled to the detecting means for obtaining a controlled operation of the detecting means during a particular time period *after the burst of concentrated light energy* to optimize the detection of the particular fluorescence during the particular time period, the particular time period having a beginning time and an ending time to enhance the detection of the *portion of the* signals representing the particular fluorescence during the particular time period relative to the portion of the signals representing the [remaining] *background* fluorescence during the particular time period, the beginning time and the ending time occurring during the production of the particular fluorescence *and the background fluorescence* from the specimen as a result of the burst of concentrated light energy, means coupled to the burst producing means, to the detecting means and to the controlling means for timing the operation of the detecting means to sequence the detection of the fluorescence from the specimen during the particular time period as a result of the production of the burst of concentrated light energy, data processing means responsive to the signals produced by the detecting means for analyzing the signals to enhance the portion of the signals representing the particular fluorescence during the particular time interval relative to the portion of the signals representing the fluorescence during the particular time interval other than the particular fluorescence, and means responsive to the [signal] *signals* from the data processing means for producing an image of the particular fluorescence.

107. The fluorometer of claim 106 wherein the means for detecting includes a photosensitive array for detecting the [fluorescence] *fluorescences* emanating from a plurality of spots on the specimen and means are included for scanning the [fluorescence] *fluorescences* from the specimen and the means for scanning includes an array control for scanning the photosensitive array to reproduce the detected [fluorescence] *fluorescences* of the different spots on the specimen.

108. The fluorometer of claim 106 wherein means are included for scanning the [fluorescence] *fluorescences* from the specimen and the means for scanning includes a stepping stage for supporting the specimen and for moving the specimen to a plurality of different positions for providing a detection of the [fluorescence] *fluorescences* emanating from the specimen at the different positions.

109. A fluorometer as set forth in claim 106 wherein the means for forming signals includes means for scanning the [fluorescence] *fluorescences* produced from the specimen during the particular time period as a result of the burst of concentrated light energy.

110. A fluorometer for measuring *the fluorescence from a specimen having a background fluorescence and* a particular fluorescence emanating from particular fluorophore molecules in [a] *the* specimen *and for distinguishing the measurement of the particular fluorescence from the measurement of the background fluorescence*, including means for producing a burst of concentrated light energy having a pulse time short compared to the decay time of the particular fluorescence and having sufficient energy to excite substantially all of the particular fluorophore molecules, means responsive to the burst of concentrated light energy for directing the burst of concentrated light energy toward the specimen to produce [fluorescence from the specimen including] the particular fluorescence *and the background fluorescence from the specimen,* means responsive to the *particular* fluorescence *and the background fluorescence* from the specimen for detecting such [fluorescence] *fluorescences* and for producing signals in accordance with such detection, means coupled to the detecting means for obtaining a controlled operation of the detecting means within a particular time period, *after the burst of the concentrated light energy,* to optimize the detection of the particular fluorescence wherein the particular time period has a beginning time and an ending time to enhance the detection of [the signals representing] the particular fluorescence during the particular time period relative to the [portion of the signals representing] *detection of* the *background* fluorescence during the particular time period [other than the particular fluorescence], the beginning and ending times occurring during the production of the particular fluorescence *and the background fluorescence* from the specimen [as a result of] *after* the burst of concentrated *light* energy, means coupled to the burst producing means, to the detecting means and to the controlling means for timing the operation of the detecting means to sequence the detection of the particular fluorescence *and the background fluorescence* from the specimen during the particular time period as a result of the production of the burst of concentrated *light* energy, *and* data processing means responsive to the signals produced by the detecting means during the particular time period for [analyzing the signals to enhance] *enhancing as a function of time* the portion of the signals representing the particular fluorescence during the particular time period relative to the portion of the signals representing the *background* fluorescence during the particular time period [other than particular fluorescence] *and for producing signals representing substantially only the particular fluorescence during the particular time period*, and means responsive to the signals from the data processing means *in representation of substantially only the particular fluorescence* for producing an image of the *particular* fluorescence.

111. The fluorometer of claim 110 wherein the means for detecting includes a photodetector for detecting the [fluorescence] *fluorescences* emanating from the specimen.

112. The fluorometer of claim [106] *110* wherein the means for detecting includes an image tube to reproduce the pattern of [fluorescence] *fluorescences* emanating from a plurality of spots on the specimen.

113. The fluorometer of claim 110 wherein the means for detecting includes a camera to analyze or record the [fluorescence] *fluorescences* emanating from a plurality of spots on the specimen.

114. The fluorometer of claim 110 wherein the means for producing the burst of concentrated light energy is a continuous wave source directing light energy through a modulator.

115. A fluorometer as set forth in claim 110, including, means for recording the particular fluorescence produced from the specimen during the particular time period as a result of the burst of concentrated light energy.

116. A fluorometer for measuring *the fluorescence from a specimen having a background fluorescence and* a particular fluorescence emanating from particular fluorophore molecules in [a] *the* specimen *and for distinguishing the measurement of the particular fluorescence from the measurement of the background fluorescence*, including means for producing a burst of concentrated light energy having a pulse time short compared to the decay time of the particular fluorescence and having sufficient energy to excite substantially all of the particular fluorophore molecules, means responsive to the burst of concentrated light energy for directing the burst of concentrated light energy toward the specimen to produce [fluorescence] *fluorescences* from the specimen including the particular fluorescence *and the background fluorescence,* means responsive to the *particular* fluorescence *and the background fluorescence* from the specimen for detecting such [fluorescence] *fluorescences* and for producing signals in accordance with such detection, means coupled to the detecting means for obtaining a controlled operation of the detecting means within a particular time period *after the burst of the concentrated light energy* to optimize the detection of the particular fluorescence wherein the *particular* time period has a beginning time and an ending time to enhance the detection of [the signals representing] the particular fluorescence during the particular time interval relative to the [portion of the signals representing] *detection of* the *background* fluorescence during the particular time period [other than the particular fluorescence], the beginning and ending times occurring during the production of the particular fluorescence *and the background fluorescence* from the specimen [as a result of] *after* the burst of concentrated light energy, means coupled to the burst producing means, to the detecting means and to the controlling means for timing the operation of the detecting means to sequence the detection of the fluorescence within the particular time period as a result of the production of the burst of concentrated light energy, data processing means responsive to the signals produced by the detecting means during the particular time period for [analysing the signals to enhance] *enhancing* the portion of the signals representing the particular fluorescence during the particular time period relative to the portion of the signals representing the *background* fluorescence during the particular time period [other than the particular fluorescence], and means responsive to the enhanced signals from the data processing means for producing an image of *substantially* the particular fluorescence during the particular time period.

117. The fluorometer of claim 116 wherein the means for detecting includes a photodetector for detecting the [fluorescence] *fluorescences* emanating from the specimen.

118. The fluorometer of claim 116 wherein the means for detecting includes an image tube to reproduce the pattern of [fluorescence] *fluorescences* emanating from a plurality of spots on the specimen.

119. The fluorometer of claim 116 wherein the means for producing the burst of concentrated light energy is a laser.

120. A fluorometer as set forth in claim 116, including, means for recording the particular fluorescence produced from the specimen during the particular time period as a result of the burst of concentrated light energy.

121. A fluorometer for measuring *the fluorescence from a specimen having a background fluorescence and* a particular fluorescence emanating from particular fluorophore molecules in [a] *the* specimen *and for distinguishing the measurement of the particular fluorescence from the measurement of the background fluorescence*, including means for producing a burst of concentrated light energy having a pulse time short compared to the decay time of the particular fluorescence and having sufficient energy to excite substantially all of the particular fluorophore molecules, means responsive to the burst of concentrated light energy for directing the burst of concentrated light energy toward the specimen to produce [fluorescence] *fluorescences* from the specimen including the particular fluorescence *and the background fluorescence,* means responsive to the *particular* fluorescence *and the background fluorescence* from the specimen for detecting such [fluorescence] *fluorescences* and for producing signals in accordance with such detection, means coupled to the detecting means for obtaining a controlled operation of the detecting means within a particular time period, *after the burst of concentrated light energy,* to optimize the detection of the particular fluorescence wherein the particular time period has a beginning time and an ending time to enhance the detection of [the signals representing] the particular fluorescence during the particular time *period* relative to the [portion of the signals representing] *detection of* the *background* fluorescence during the particular time period [other than the particular fluorescence], the beginning and ending times occurring during the production of the particular fluorescence *and the background fluorescence,* means coupled to the burst producing means, to the detecting means and to the controlling means for timing the operation of the detecting means to sequence the detection of the fluorescence during the particular time period [as a result of] *after* the production of the burst of concentrated light energy, *and* data processing means responsive to the signals produced by the detecting means during the particular time period for [analyzing the signals to enhance] *enhancing* the portion of the signals representing the particular fluorescence during the particular time period relative to the portion of the signals representing the *background* fluorescence during the particular time period [other than the particular fluorescence], and the means for controlling the [passage of the image] *detection of the fluorescences* constituting an electro-optic modulator formed by a cubic crystal of the class $T_d$.

122. The fluorometer of claim 121 wherein the cubic crystal of the class $T_d$ is cuprous chloride.

123. The fluorometer of claim 121 wherein the electro-optic modulator is formed from at least one of the following group of materials:

CuCl (Cuprous chloride)
CuBr (Cuprous bromide)
CuI (Cuprous iodide)
ZnS (Zinc sulfide)
ZnSe (Zinc selenide)
ZnTe (Zinc telluride)
$(CH_2)_6N_4$ (Hexamine or Hexamethylenetetramine)
$(Na, Ca)_{8-4}(SO_4)_{2-1}[(AlSiO_4)_6]]$(Hauynite)
GaP (Gallium phosphide)
$Bi_4(GeO_4)_3$ (Bismuth germanate)
$NaClO_3$ (Sodium chlorate)
$BaTiO_3$ (Barium titanate)
$SrTiO_3$ (Strontium titanate)
$KTaO_3$ (Potassium tantalate)
$KTa_xNb_{1-x}O_3$ (Potassium tantalate niobate)

* * * * *